United States Patent
Okubo et al.

(10) Patent No.: US 7,569,259 B2
(45) Date of Patent: Aug. 4, 2009

(54) PLASTICIZER, CELLULOSE ESTER FILM, POLARIZING PLATE, AND LIQUID CRYSTAL DISPLAY

(75) Inventors: Yasushi Okubo, Hino (JP); Kazuto Kiyohara, Kokubunji (JP); Satomi Kawabe, Hachioji (JP); Akihiko Takeda, Sagamiko-machi (JP); Takayuki Suzuki, Hachioji (JP); Kazuaki Nakamura, Tokyo (JP)

(73) Assignee: Konica Minolta Opto, Inc., Tokyo (JP)

( * ) Notice: Subject to any disclaimer, the term of this patent is extended or adjusted under 35 U.S.C. 154(b) by 373 days.

(21) Appl. No.: 11/294,493

(22) Filed: Dec. 6, 2005

(65) Prior Publication Data

US 2006/0127607 A1  Jun. 15, 2006

(30) Foreign Application Priority Data

Dec. 9, 2004  (JP) .............................. 2004-356546
Nov. 10, 2005 (JP) .............................. 2005-326178

(51) Int. Cl.
*C08K 5/103* (2006.01)
*C08L 1/14* (2006.01)

(52) U.S. Cl. .................... 428/1.33; 428/1.54; 106/170.3
(58) Field of Classification Search .................. 428/1.3, 428/1.31, 1.54; 524/306, 315; 106/170.3
See application file for complete search history.

(56) References Cited

U.S. PATENT DOCUMENTS

| | | | | | |
|---|---|---|---|---|---|
| 2,036,271 | A | * | 4/1936 | Hahn | 106/107.3 |
| 2,147,697 | A | * | 2/1939 | Gloor | 524/39 |
| 2,213,783 | A | * | 9/1940 | Kyrides | 560/52 |
| 3,279,990 | A | * | 10/1966 | Rose et al. | 514/25 |
| 3,470,099 | A | * | 9/1969 | Burkard et al. | 508/483 |
| 3,814,729 | A | * | 6/1974 | Gouch | 524/292 |
| 3,850,663 | A | * | 11/1974 | Hagenbach | 430/111.2 |
| 3,988,446 | A | * | 10/1976 | Paris et al. | 514/159 |
| 4,342,875 | A | * | 8/1982 | Gough | 560/64 |
| 2003/0097963 | A1 | * | 5/2003 | Schunk et al. | 106/170.11 |
| 2006/0078754 | A1 | * | 4/2006 | Murakami et al. | 428/532 |

FOREIGN PATENT DOCUMENTS

JP  2000352620 A  *  12/2000
JP  2003232926 A  *  8/2003

OTHER PUBLICATIONS

JPO Website Machine English Translation of JP 2004-323749, Shibuya Masahiro, Nov. 18, 2004.*
JPO Website Machine English Translation of JP 2000-352620, Murakami et al., Dec. 19, 2000.*
JPO Website Machine English Translation of JP 2003-232926, Saito et al., Aug. 22, 2003.*

* cited by examiner

*Primary Examiner*—Keith D Hendricks
*Assistant Examiner*—Sophie Hon
(74) *Attorney, Agent, or Firm*—Finnegan, Henderson, Farabow, Garrett & Dunner, L.L.P.

(57) ABSTRACT

A plasticizer comprising an ester compound produced by a condensation reaction of an organic acid represented by Formula (1) with a polyhydric alcohol having at least 3 hydroxyl groups in the molecule,

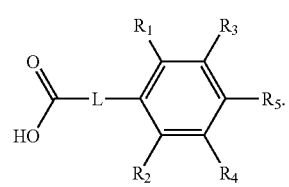

Formula (1)

9 Claims, No Drawings

PLASTICIZER, CELLULOSE ESTER FILM, POLARIZING PLATE, AND LIQUID CRYSTAL DISPLAY

This application is based on Japanese Patent Application No. 2004-356546 filed on Dec. 9, 2004 and No. 2005-326178 filed on Nov. 10, 2005 in Japanese Patent Office, the entire content of which is hereby incorporated by reference.

TECHNICAL FIELD

The present invention relates to a plasticizer, a cellulose ester optical film, a polarizing plate employing the above cellulose ester film, and a liquid crystal display.

BACKGROUND

Cellulose ester film has been employed as a photographic negative film support, and in polarizing plates as a film which protects polarizers employed in liquid crystal displays, due to its high transparency, low birefringence, and ease of adhesion to polarizers.

In recent years, the production amount of liquid crystal displays has markedly increased due to the thin depth and light weight, and the demand is increasing. Further, television sets, which employ a liquid crystal display, exhibit features such as thinness and light weight. Thereby, large-sized television sets, production of which was not possible by employing Braun tubes, have been produced. Along with that trend, demand for polarizers and polarizer protecting films has been increasing.

Heretofore, these cellulose ester films have been produced mainly employing a solution-casting method. The solution-casting method, as descried herein, refers to a film forming method in which a solution prepared by dissolving cellulose ester in solvents is cast to form film and solvents are evaporated and dried to produce film. The film which is cast employing the solution-casting method exhibits high flatness, whereby by employing the resulting film, it is possible to produce uniform and high image quality liquid crystal displays.

However, an inherent problem of the solution-casting method is the necessity of a large volume of organic solvents followed by a high environment load. The cellulose ester film is cast employing halogen based solvents which result in a high environment load, due to its solubility characteristics. Consequently, it has particularly demanded to reduce the amount of used solvents, whereby it has been difficult to increase the production of cellulose ester film employing the solution-casting method.

Accordingly, in recent years, experiments have been conducted in which cellulose ester is subjected to melt-casting for the use of silver salt photography (Patent Document 1) and as a polarizer protective film (Patent Document 2). However, cellulose ester is a polymer which exhibits a very high viscosity when melted and also exhibits a very high glass transition point. As a result, when cellulose ester is melted, extruded from a die and cast onto a cooling drum or belt, it is difficult to achieve leveling, and after extrusion, solidification occurs in a relatively short time, whereby a major problem has been that flatness of the resulting film is inferior to that of the a solution-casting film.

In order to lower the melt viscosity and glass transition point of organic polymers such as cellulose ester, it is known that addition of plasticizers is effective.

In above Patent Documents 1 and 2, employed are phosphoric acid plasticizers such as triphenyl phosphate or phenylenebisdiphenyl phosphate. However, the result of investigations conducted by the inventors of the present invention has clarified that in these phosphoric acid plasticizers, phosphoric acid esters undergo decomposition due to moisture sorption or heating, resulting in generation of phosphoric acid, whereby problems occur in which generated phosphoric acid degrades cellulose ester and a film is stained.

In the solution-casting, known as plasticizers, other than phosphoric acid esters, which are employed in cellulose ester, are ethylene glycol based plasticizers or polyhydric alcohol based esters which are esters of trihydric or higher alcohol with carboxylic acids. For example, Patent Document 3 discloses glycerin-carboxylic acid based esters, Patent Document 4 discloses diglycerin-carboxylic acid esters, Patent Document 5 discloses pentaerythritol or dipentaerythritol based esters, and Patent Document 6 discloses sugar alcohol based esters such as sorbitol. Plasticizers composed of polyhydric alcohol-carboxylic acid exhibit relatively high chemical stability, and even when hydrolyzed, do not generate strong acids which degrade cellulose ester, whereby they are preferable plasticizers for casting of cellulose ester. However, most of them are alkyl ester based, resulting in insufficient effects to lower water vapor permeability. Further, Patent Document 7 discloses polyhydric alcohol-aromatic carboxylic acid and polyhydric alcohol-cycloalkylcarboxylic acid based esters. However, it has been found that such compounds having a ring structure result in insufficient effects to lower viscosity as a plasticizer during melt-casting of cellulose ester, whereby problems occur in which it is not possible to prepare cellulose ester films which exhibit flatness.

Further, there was a problem of bleeding out of a plasticizer, i.e., deposition or evaporation of a plasticizer getting out of the film.

Further, in any of Patent Documents 3-7, described are neither specific synthesis examples nor specific compounds of aromatic esters having a substituent, and no effects of having the substituent are also described. In addition, no description is made for the application of these plasticizers to a melt-cast cellulose ester film.

(Patent Document 1) Japanese Patent Publication Open to Public Inspection (under PCT Application) No. 6-501040

(Patent Document 2) Japanese Patent Publication Open to Public Inspection (hereinafter referred to as JP-A) No. 2000-352620

(Patent Document 3) JP-A No. 11-246704
(Patent Document 4) JP-A No. 2000-63560
(Patent Document 5) JP-A No. 11-124445
(Patent Document 6) JP-A No. 2001-247717
(Patent Document 7) JP-A No. 2003-12823

SUMMARY

Consequently, an object of the present invention is to provide a plasticizer which can decrease the viscosity and does not show the problem of deposition or evaporation of a plasticizer getting out of the film. Another object f the present invention is to provide a cellulose ester film of high flatness and decreased bleeding out of a plasticizer, employing a melt-casting film forming method which does not employ halogen based solvents, which result in a large environment load, and further to provide a polarizing plate of high uniformity and liquid crystal displays of high image quality.

In view of the foregoing problems, the inventors of the present invention conducted diligent investigation, and discovered the following, thereby achieving the present invention. Ester compounds which have a structure formed by condensing aromatic carboxylic acid substituted with a specified substituent with polyhydric alcohol were chemically stable, capable of decreasing the viscosity and bleeding out of a plasticizer, and exhibited high compatibility with cellulose ester. By employing the above compounds as a plasticizer, it was possible to prepare cellulose ester which exhibited high flatness even when a melt-casting method was employed.

Namely, it was possible to solve the above problems employing the following embodiments.

(1) One of the embodiments of the present invention includes a plasticizer comprising an ester compound produced by a condensation reaction of an organic acid represented by Formula (1) with a polyhydric alcohol having at least 3 hydroxyl groups in the molecule,

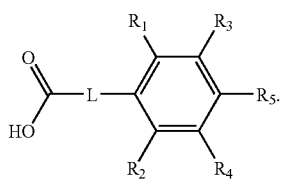

Formula (1)

wherein $R_1$ to $R_5$ are each independently represent a hydrogen atom, a cycloalkyl group, an aralkyl group, an alkoxy group, a cycloalkoxy group, an aryloxy group, an aralkyloxy group, an acyl group, a carbonyloxyl group, an oxycarbonyl group or an oxycarbonyloxy group, provided that $R_1$ to $R_5$ may have further a substituent and at least one of $R_1$ to $R_5$ is not a hydrogen atom; and L is a single bond or a linking group selected from the group consisting of a alkylene group which may have a substituent and an oxygen atom.

(2) Another embodiment of the present invention includes a plasticizer of the above-described item 1, wherein the polyhydric alcohol has 3 or 4 hydroxyl groups in the molecule.

(3) Another embodiment of the present invention includes a plasticizer of the above-described item 1, wherein a molecular weight of the ester compound is 400 to 1000.

(4) Another embodiment of the present invention includes a plasticizer of the above-described item 1, wherein at least one of $R_1$ to $R_5$ of Formula (1) is selected from the group consisting of an alkoxy group, an acyl group, an oxycarbonyl group, a carbonyloxyl group and an oxycarbonyloxy group.

(5) Another embodiment of the present invention includes a plasticizer of the above-described item 1, further represented by Formula (2),

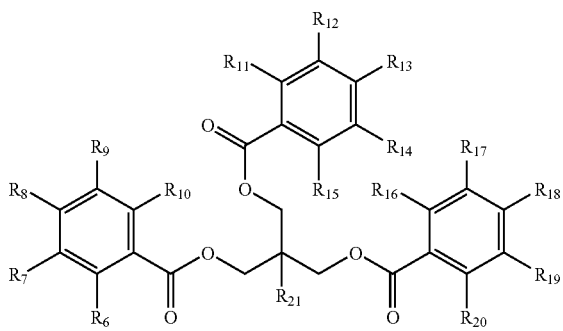

Formula (2)

wherein $R_6$ to $R_{20}$ are each independently represent a hydrogen atom, a cycloalkyl group, an aralkyl group, an alkoxy group, a cycloalkoxy group, an aryloxy group, an aralkyloxy group, an acyl group, a carbonyloxyl group, an oxycarbonyl group or an oxycarbonyloxy group, provided that $R_6$ to $R_{20}$ may have further a substituent and at least one of $R_6$ to $R_{10}$, at least one of $R_{11}$ to $R_{15}$ and at least one of $R_{16}$ to $R_{20}$ each is not a hydrogen atom; and $R_{21}$ represents an alkyl group.

(6) Another embodiment of the present invention includes a cellulose ester film comprising the plasticizer of the above-described item 1 in an amount of 1 to 25 weight % based on the total weight of the cellulose ester film.

(7) Another embodiment of the present invention includes a cellulose ester film of the above-described item 6, satisfying the following Relationship (2) and Relationship (3), $$2.5 \leq X+Y \leq 2.9$$ Relationship (2)

$$0.1 \leq Y \leq 2.0$$ Relationship (3)

wherein X is a degree of substitution with acetic acid and Y is a degree of substitution with an aliphatic acid having 3 to 5 carbon atoms.

(8) Another embodiment of the present invention includes a cellulose ester film of the above-described item 6, produced by a melt casting film forming method.

(9) Another embodiment of the present invention includes a cellulose ester film of the above-described item 6, further comprising an anti-oxidation agent in the film.

(10) Another embodiment of the present invention includes a cellulose ester film of the above-described item 6, further comprising an acid scavenger in the film.

(11) Another embodiment of the present invention includes a cellulose ester film of the above-described item 6, further comprising an UV absorbing agent in the film.

(12) Another embodiment of the present invention includes a polarizing plate comprising the cellulose ester film of the above-describe item 6 as a protective film on the polarizing plate.

(13) Another embodiment of the present invention includes a liquid crystal display comprising the polarizing plate of the above-described item 12.

Based on the present invention, it is impossible to provide plasticizers which are capable of decreasing the viscosity and exhibit high compatibility with cellulose ester and markedly lower bleeding out. By employing the above plasticizers, it is possible to provide cellulose ester films and polarizing plates which exhibit preferred optical characteristics, dimensional stability, and flatness. Further, by employing the above polarizing plates, it is possible to produce high image quality liquid crystal displays. Still further, it is possible to provide the above cellulose ester film employing a melt-casting method which does not require halogen based solvents exhibiting a high environment load.

DESCRIPTION OF THE PREFERRED EMBODIMENTS

The most preferred embodiments to achieve the present invention will now be described, however the present invention is not limited thereto.

The present invention makes it possible to prepare a new plasticizer and cellulose ester films which exhibit desired flatness, as well as excellent optical characteristics and dimensional stability, even employing cellulose resins which have been subjected to melt-casting.

By employing the above cellulose ester film, it is possible to produce an optical film such as a high quality polarizing plate protecting film, an antireflection film, or a retardation film, and further to produce liquid crystal displays exhibiting a high display quality.

The inventors of the present invention conducted diligent investigations and discovered the following. In order to produce cellulose ester films which exhibit excellent optical characteristics and dimensional stability as well as desired flatness, in a casting method of a heat-melt method, namely in film casting employing a melt-casting method, which does not use halogen based solvents of a high environment load, the flatness of the resulting cellulose ester films was markedly enhanced by selecting some specific compounds as a plasticizer incorporated in the cellulose esters.

Namely, in the melt-casting method in which melted cellulose ester was cast onto a cooling drum or belt, it was discovered that by employing the plasticizers according to the present invention, leveling was easily achieved, whereby a film of high flatness was easily produced.

The cellulose ester film of the present invention is characterized in incorporating, as a plasticizer in an amount of 1-25 percent by weight, ester compounds having a structure which is formed by condensing organic acids represented by above Formula (1), and polyhydric alcohols having 3 OH groups or more in the molecule. When the above amount is at most 1 percent by weight, no advantageous effects to improve flatness result, while when it exceeds 25 percent by weight, bleeding-out tends to occur to degrade storage stability of the film, both neither of which are desired. The cellulose ester film is more preferred which incorporates the plasticizers in an amount of 3-20 percent by weight, and is still more preferred which incorporates the plasticizers in an amount of 5-15 percent by weight.

Plasticizers, as described herein, commonly refer to additives which decrease brittleness and result in enhanced flexibility upon being incorporated in polymers. In the present invention, plasticizers are added so that the melting temperature of a cellulose ester resin is lowered, and at the same temperature, the melt viscosity of a cellulose ester resin is lower than that of film constituting materials incorporating plasticizers. Further, addition is performed to enhance hydrophilicity of cellulose ester so that the water vapor permeability of cellulose ester films is improved. Therefore, the plasticizers of the present invention have a property of decreasing a water vapor permeability.

The melting temperature of film constituting materials, as described herein, refers to the temperature at which the above materials are heated to result in a state of fluidity. In order that cellulose ester results in melt fluidity, it is necessary to heat cellulose ester to a temperature which is at least higher than the glass transition temperature. At or above the glass transition temperature, the elastic modulus or viscosity decreases due to heat absorption, whereby fluidity results. However, at higher temperatures, cellulose ester melts and simultaneously undergoes thermal decomposition to result in a decrease in the molecular weight of the cellulose ester, whereby the dynamical characteristics of the resulting film may be adversely affected. Consequently, it is necessary to melt cellulose ester at a temperature as low as possible. Lowering the melting temperature of film constituting materials is achieved by the addition of plasticizers, which exhibit a melting point which is equal to or lower than the glass transition temperature. Polyhydric alcohol ester based plasticizers, which have a structure which is formed by condensing the organic acid represented by above Formula (1) and polyhydric alcohol, lower the melting temperature of the cellulose ester and exhibit preferred process adaptability due to minimal volatility during the melt-casting process and after production. Further, optical characteristics, dimensional stability, and flatness of the resulting polyester films are improved.

In above Formula (1), $R_1$-$R_5$ each represent a hydrogen atom, an alkyl group, a cycloalkyl group, an aryl group, an aralkyl group, an alkoxy group, a cycloalkoxy group, an aryloxy group, an aralkyloxy group, an acyl group, a carbonyloxy group, an oxycarbonyl group, or an oxycarbonyloxy group, any of which may be further substituted. None of $R_1$-$R_6$ represent a hydrogen atom. L represents a divalent linking group, which includes a substituted or unsubstituted alkylene group, an oxygen atom or a direct bond.

Listed as alkyl groups are, for example, a methyl, ethyl, propyl, 2-ethylhexyl, octyl, dodecyl or octadecyl group. However, since cellulose ester is a relatively hydrophilic polymer, the introduction of an excessively higher aliphatic group as a substituent occasionally degrades compatibility with cellulose ester, whereby an alkyl group having 1-8 carbon atoms is preferred. Further, these groups may be substituted. Listed as preferred substituents are a halogen atom such as a chlorine atom, a bromine atom, or a fluorine atom. A hydroxyl group, an alkoxy group, a cycloalkoxy group, a phenyl group (this phenyl group may further be substituted with an alkyl group or a halogen atom), an aryloxy group (for example, a phenoxy group (this phenyl group may further be substituted with an alkyl group or a halogen atom)), an acetyl group, an acyl group having 2-8 carbon atoms such as a propionyl group, and a carbonyloxy group having 2-8 carbon atoms such as an acetyloxy group or a propionyloxy group.

Also preferred as the cycloalkyl group represented by $R_1$-$R_5$ is a cycloalkyl group having 3-8 carbon atoms, and specific examples include cyclopropyl, cyclopentyl and cyclohexyl groups. These groups may be substituted. Listed as preferred substituents are a halogen atom such as a chlorine atom or a bromine atom, a hydroxyl group, an alkyl group, an alkoxy group, an aralkyl group (this phenyl group may further be substituted with a halogen atom), a vinyl group, an alkenyl group such as an aryl group, a phenyl group (this phenyl group may further be substituted with an alkyl group, or a halogen atom), a phenoxy group (this phenyl group may further be substituted with an alkyl group or a halogen atom), an acetyl group, an acyl group having 2-8 carbon atoms such as a propionyl group, an acetyloxy group, or a non-substituted carbonyloxy group having 2-8 carbon atoms such a propionyloxy group.

The aralkyl group represented by $R_1$-$R_5$ includes a benzyl group, a phenetyl group, and a γ-phenylpropyl group, which may be substituted. Listed as the preferred substituents may be those which may be substituted for the above cycloalkyl group.

The alkoxy group represented by $R_1$-$R_5$ include an alkoxy group having 1-8 carbon atoms. The specific examples include an methoxy group, an ethoxy group, an n-propoxy group, an n-butoxy group, an n-octyloxy group, an isopropoxy group, an isobutoxy group, a 2-ethylhexyloxy group, or a t-butoxy group, which may be substituted. Listed as preferred substituents may, for example, be a chlorine atom, a bromine atom, a fluorine atom, a hydroxyl group, an alkoxy group, a cycloalkoxy group, an aralkyl group (this phenyl group may be substituted with an alkyl group or a halogen atom), an alkenyl group, a phenyl group (this phenyl group may further be substituted with an alkyl group or a halogen atom), an aryloxy group (for example, a phenoxy group (this phenyl group may further be substituted with an alkyl group or a halogen atom)), an acetyl group, an acyl group such as a propionyl group, an acyloxy group such as a propionyloxy group having 2-8 carbon atoms, or an arylcarbonyloxy group such as a benzoyloxy group.

The cycloalkoxy groups represented by $R_1$-$R_5$ include an cycloalkoxy group having 1-8 carbon atoms as an unsubstituted cycloalkoxy group. Specific examples include a cyclopropyloxy, cyclopentyloxy and cyclohexyloxy group, which may be substituted. Listed as the preferred substituents may be those may be substituted to the above cycloalkyl group.

The aryloxy groups represented by $R_1$-$R_5$ include a phenoxy group having 1-8 carbon atoms as an unsubstituted cycloalkoxy group. This phenyl group may be substituted with the substituent listed as a substituent such as an alkyl group or a halogen atom which may substitute to the above cycloalkyl group.

The aralkyloxy group represented by $R_1$-$R_6$ includes a benzoyloxy group, which may further be substituted. Listed as the preferred substituents may be those which may be substituted for the above cycloalkyl group.

The acyl group represented by $R_1$-$R_5$ includes an unsubstituted acyl group having 1-8 carbon atoms such as an acetyl group (an alkyl, alkenyl, or alkynyl group is included as a hydrocarbon group of the acyl group), which may further be substituted. Listed as the preferred substituents may be those which may be substituted for the above cycloalkyl group.

The carbonyloxy group represented by $R_1$-$R_5$ includes an unsubstituted acyloxy group (an alkyl, alkenyl, or alkynyl group is included as a hydrocarbon group of the acyl group) having 2-8 carbon atoms such as an acetyloxy group or an arylcarbonyloxy group such as a benzoyloxy group, which may be substituted with the group which may be substituted for the above cycloalkyl group.

The oxycarbonyl group represented by $R_1$-$R_6$ includes an alkoxycarbonyl group such as a methoxycarbonyl group, an ethoxycarbonyl group, or a propyloxycarbonyl group, which may further be substituted. Listed as the preferred substituents may be those which may be substituted for the above cycloalkyl group.

The oxycarbonyloxy group represented by $R_1$-$R_5$ includes an alkoxycarbonyloxy group such as a methoxycarbonyloxy group, which may further be substituted. Listed as the preferred substituents may be those which may be substituted for the above cycloalkyl group.

Further, at least one of $R_1$-$R_5$ is not a hydrogen atom. Further, some of $R_1$-$R_5$ may link to each other to form a ring structure.

Further, the linking group represented by L includes a substituted or unsubstituted alkylene group, an oxygen atom, or a direct bond. The alkylene group includes a methylene group, an ethylene group, and a propylene group, which may be substituted with the substituent which is substituted for the group represented by above $R_1$-$R_5$.

Of these, one which is particularly preferred as the linking group is the direct bond which is an aromatic carboxylic acid.

Further, preferred as the organic acids represented by above Formula (1), which constitute ester compounds which are plasticizers in the present invention, and are those which posses the above alkoxy group, acyl group, oxycarbonyl group, carbonyloxy group or oxycarbonyloxy group in either $R_1$ or $R_2$.

Further, the organic acids represented by above Formula (1) may contain a plurality of substituents.

In the present invention, organic acids which substitute the hydroxyl group of polyhydric alcohol having 3 OH groups or more in the molecule may be either a single kind or a plurality of them.

In the present invention, as polyhydric compounds which react with the organic acid represented by above Formula (1) to form polyhydric alcohol esters are preferably aliphatic polyhydric alcohols such as alcohols having 3 to 20 hydroxyl groups in the molecule. In the present invention, preferred as polyhydric alcohols are those represented by Formula (3) below.

$$R'—(OH)_m \qquad \text{Formula (3)}$$

wherein R' represents a m-valent organic group, m represents an integer at least 3, and the OH group represents a hydroxyl group. Particularly preferred are polyhydric alcohols of m of 3 or 4.

Examples of preferred polyhydric alcohols include, but are not limited to, adonitol, arabitol, 1,2,4-butanetriol, 1,2,3-hexanetriol, 1,2,6-hexanetriol, glycerin, diglycerin, erythritol, pentaerythritol, dipentaerythritol, tripentaerythritol, galactitol, glucose, cellobiose, inositol, mannitol, 3-methylpentane-1,3,5-triol, pinacol, sorbitol, trimethylolpropane, trimethylolethane, and xylitol. Particularly preferred are glycerin, trimethylolethane, trimethylolpropane, and pentaerythritol.

It is possible to synthesize esters of the organic acid represented by Formula (1) and polyhydric alcohol having 3 OH groups or more in the molecule, employing methods known in the art. A representative synthesis example is shown in the examples. One method is in which the organic acid represented by the above Formula (1) and polyhydric alcohol undergo etherification via condensation in the presence of, for example, acids, and another method is in which organic acid is converted to acid chloride or acid anhydride which is allowed to react with polyhydric alcohol, and still another method is in which the phenyl ester of organic acid is allowed to react with polyhydric alcohol. Depending on the targeted ester compound, it is preferable to select an appropriate method which results in a high yield.

The plasticizer represented by Formula (1) is preferably represented by Formula (2) below.

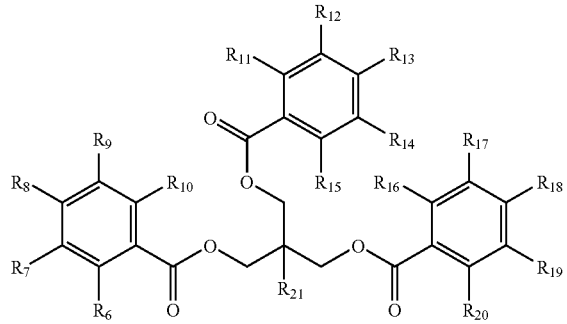

Formula (2)

wherein $R_6$ to $R_{20}$ are each independently represent a hydrogen atom, a cycloalkyl group, an aralkyl group, an alkoxy group, a cycloalkoxy group, an aryloxy group, an aralkyloxy group, an acyl group, a carbonyloxyl group, an oxycarbonyl group or an oxycarbonyloxy group, provided that $R_6$ to $R_{20}$ may have further a substituent and at least one of $R_6$ to $R_{10}$, at least one of $R_{11}$ to $R_{15}$ and at least one of $R_{16}$ to $R_{20}$ each is s not a hydrogen atom; and $R_{21}$ represents an alkyl group.

The above described cycloalkyl group, aralkyl group, alkoxy group, cycloalkoxy group, aryloxy group, aralkyloxy group, acyl group, carbonyloxyl group, oxycarbonyl group and oxycarbonyloxy group represented by $R_6$ to $R_{20}$ indicate the same as groups of $R_1$ to $R_5$ in Formula (1).

The molecular weight of the polyhydric alcohol esters prepared as above is not particularly limited, but is preferably 300-1,500, but is more preferably 500-1,000. A greater molecular weight is preferred due to reduced volatility, while a smaller molecular weight is preferred in view of the resulting water vapor permeability and compatibility with cellulose ester.

Specific compounds of polyhydric alcohol esters according to the present invention will now be exemplified.

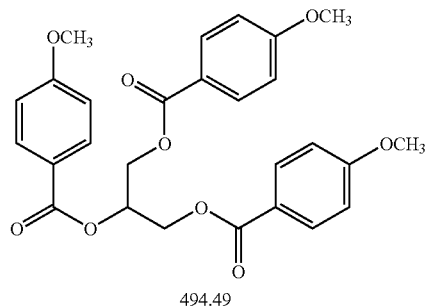
494.49
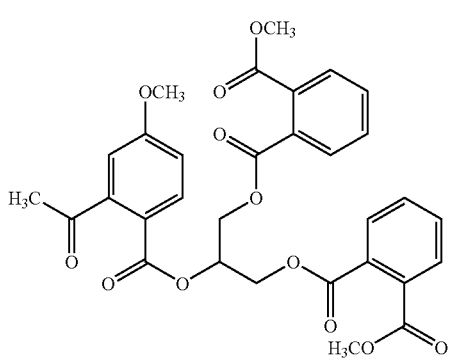
578.52
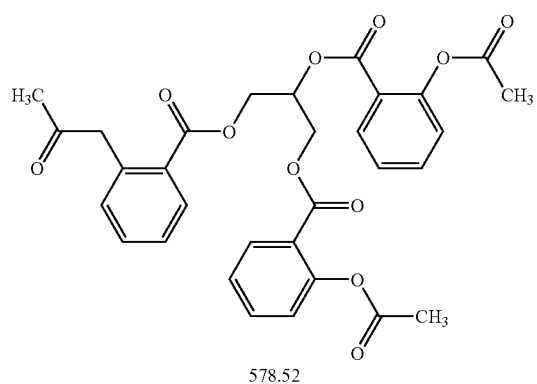
578.52
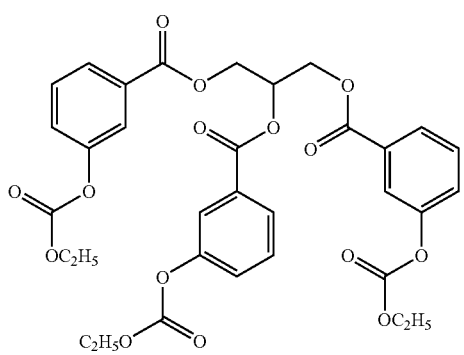
668.60
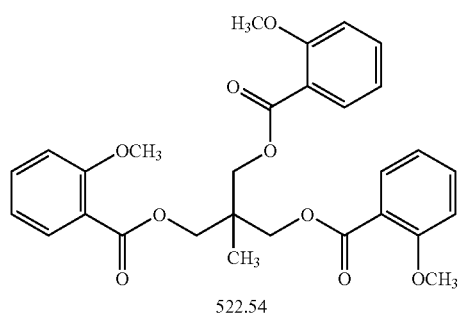
522.54
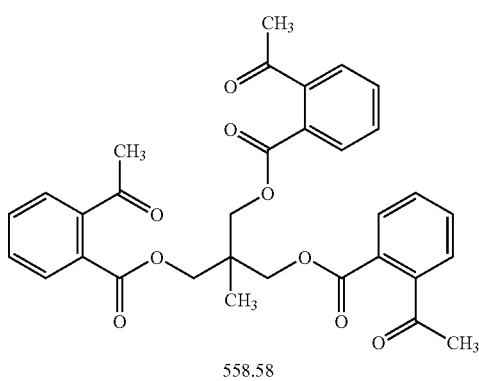
558.58
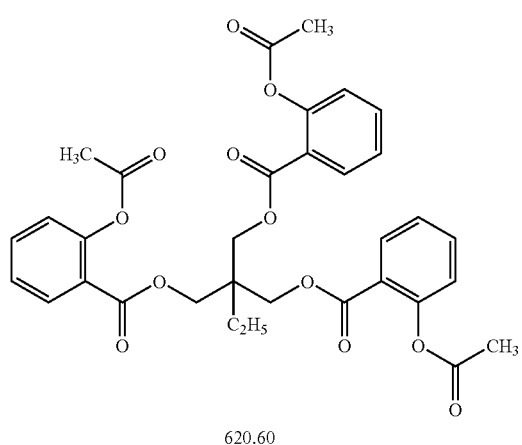
620.60
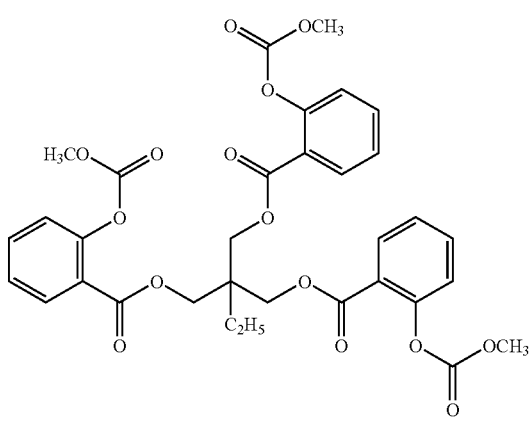
668.60

-continued
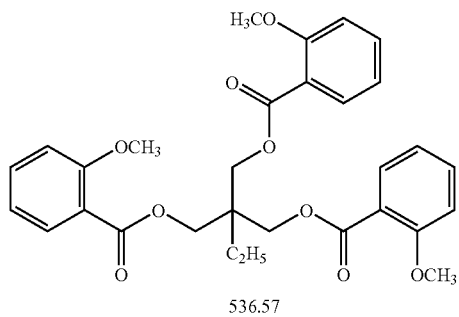
536.57
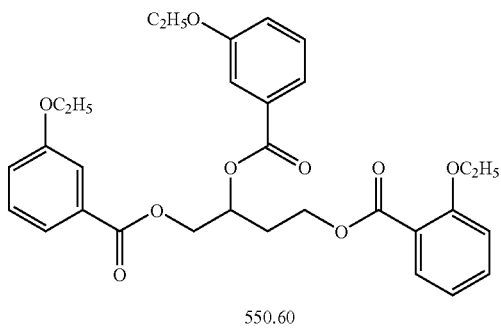
550.60
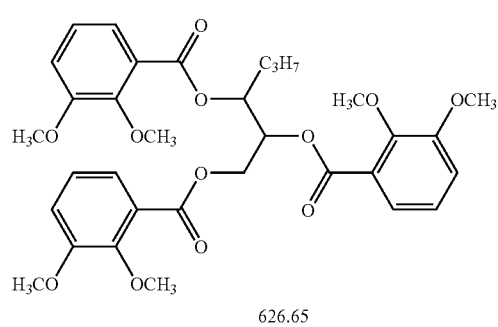
626.65
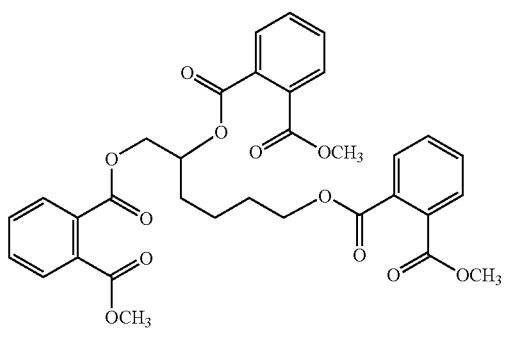
620.60
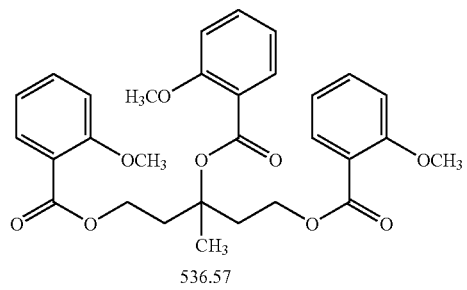
536.57
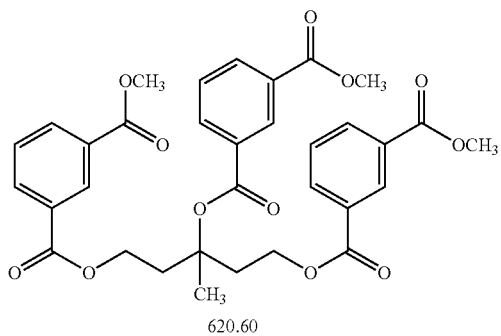
620.60
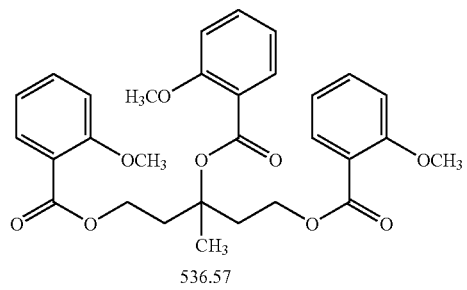
770.69
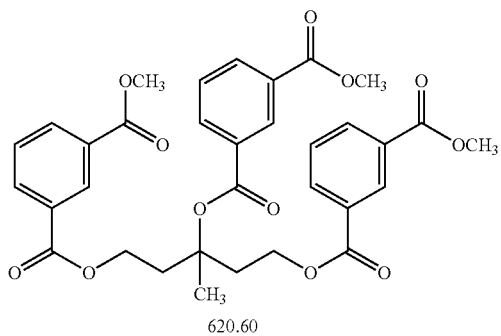
702.70

-continued
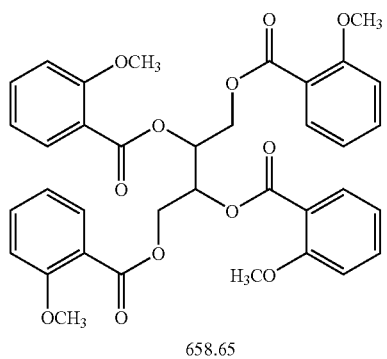
17
658.65
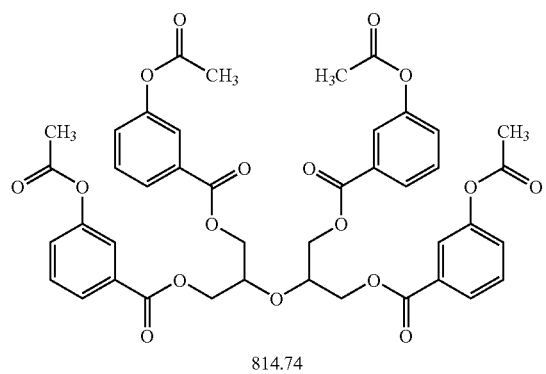
18
814.74
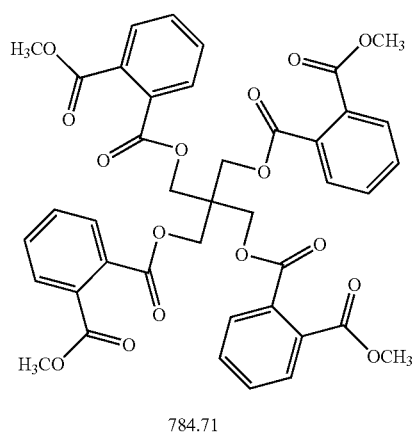
19
784.71
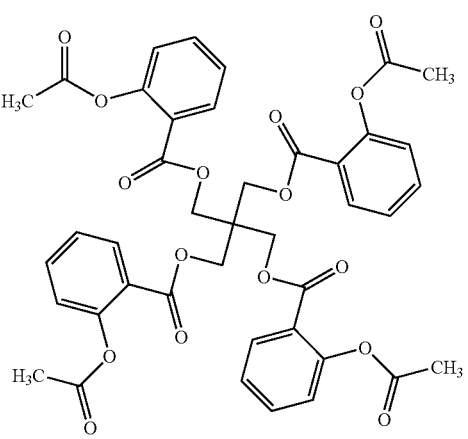
20
784.71
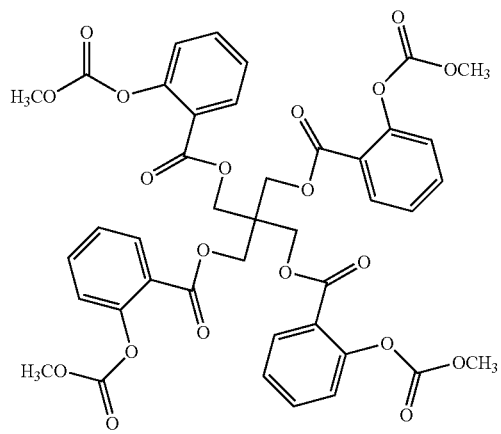
21
848.71
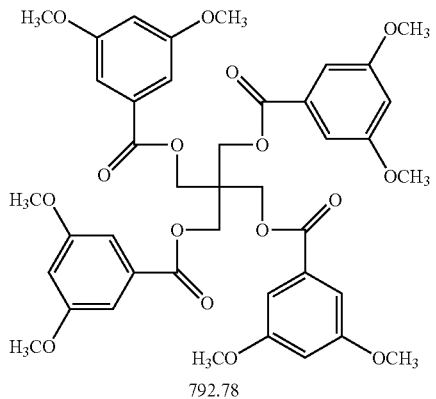
22
792.78

23
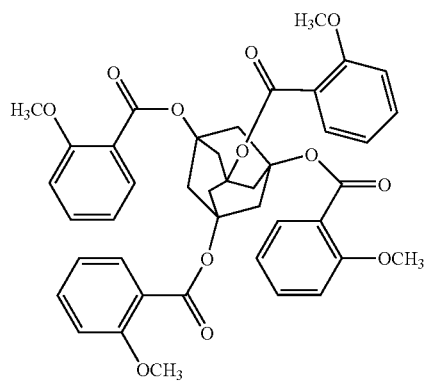
736.76
24
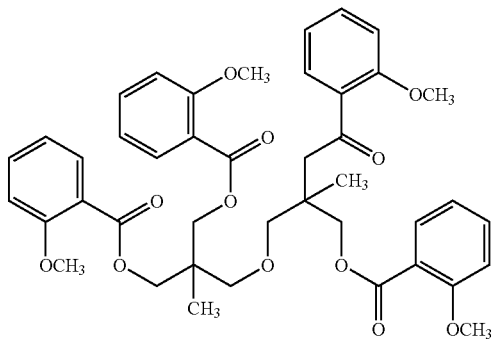
742.81
25
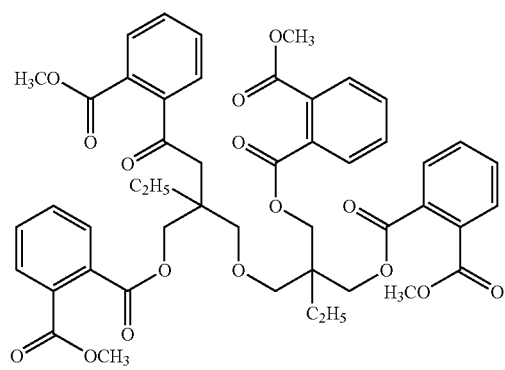
882.90
26
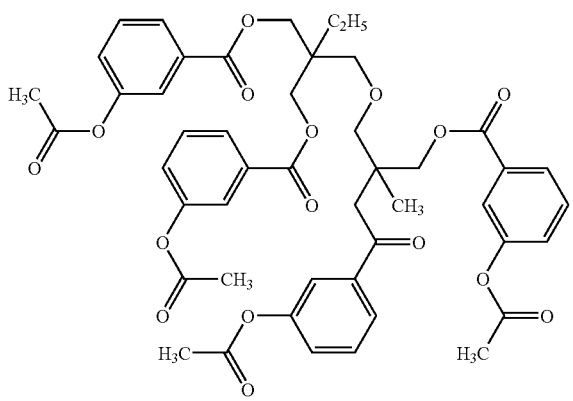
868.87
27
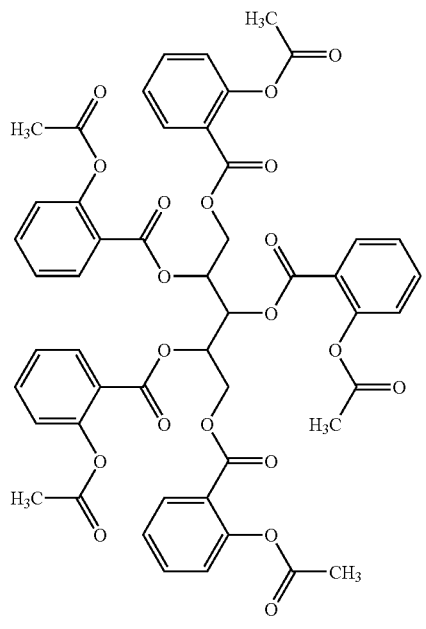
962.86
28
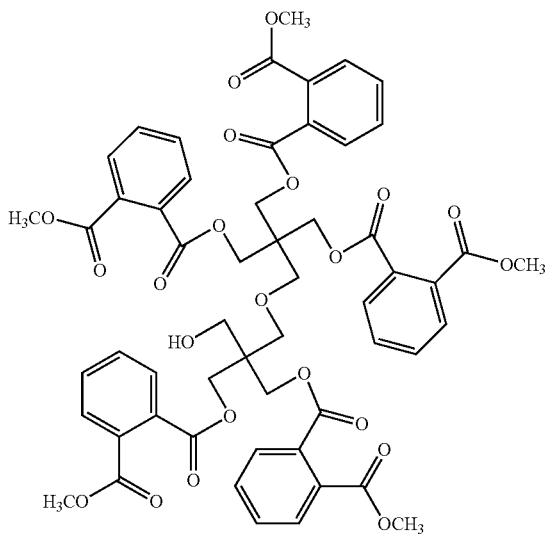
1064.99

-continued
29
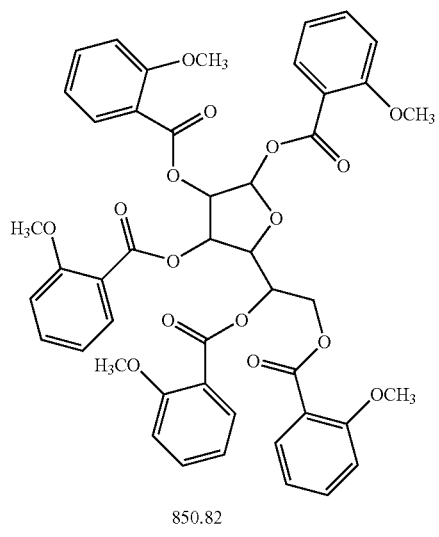
850.82
30
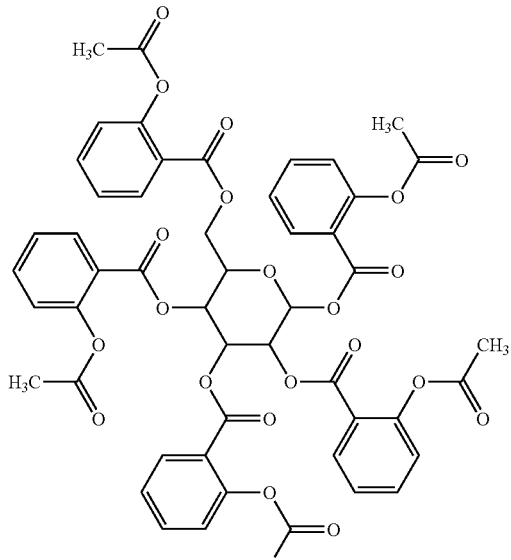
990.87
31
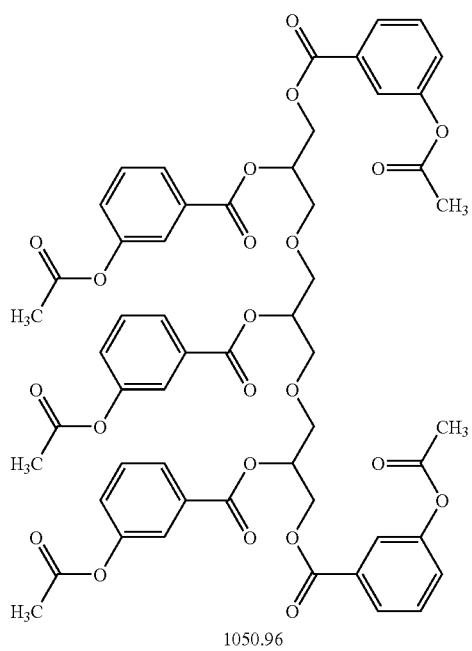
1050.96
32
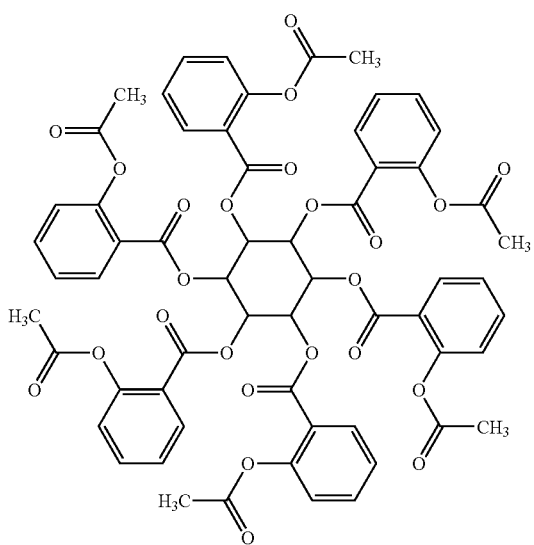
1153.01

-continued
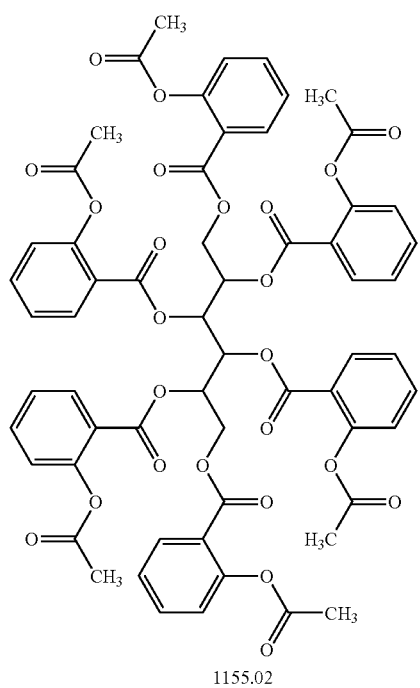
1155.02
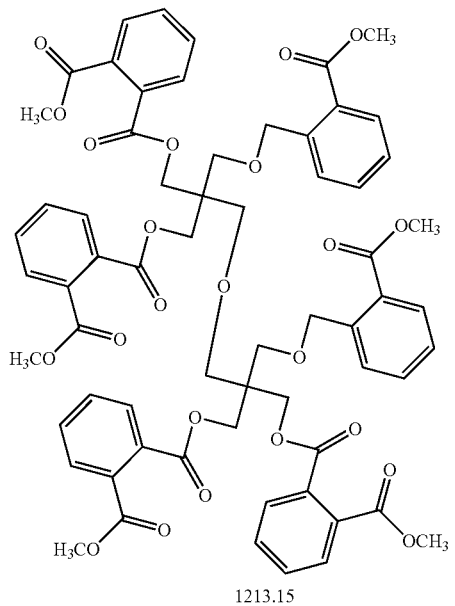
1213.15
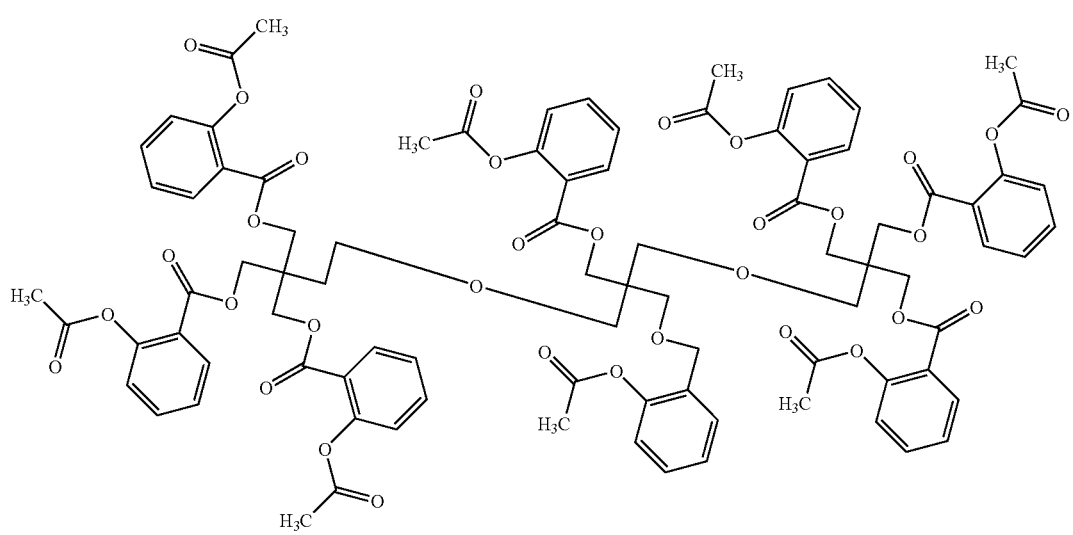
1669.59

-continued
36
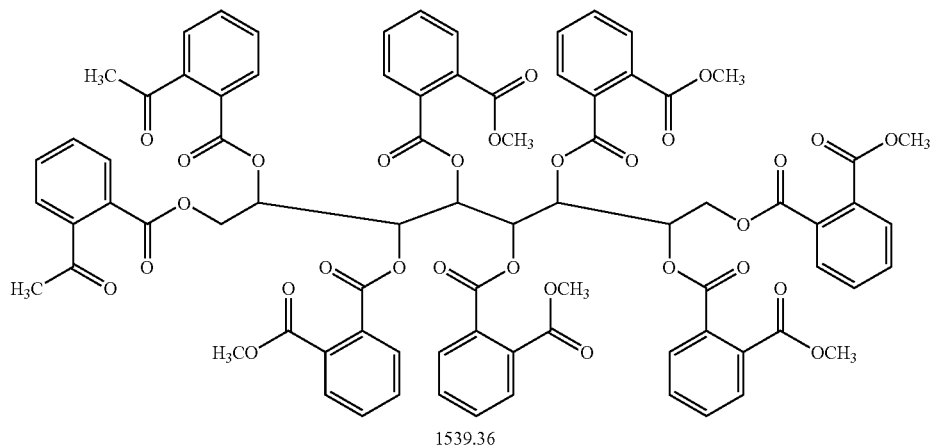
1539.36
37
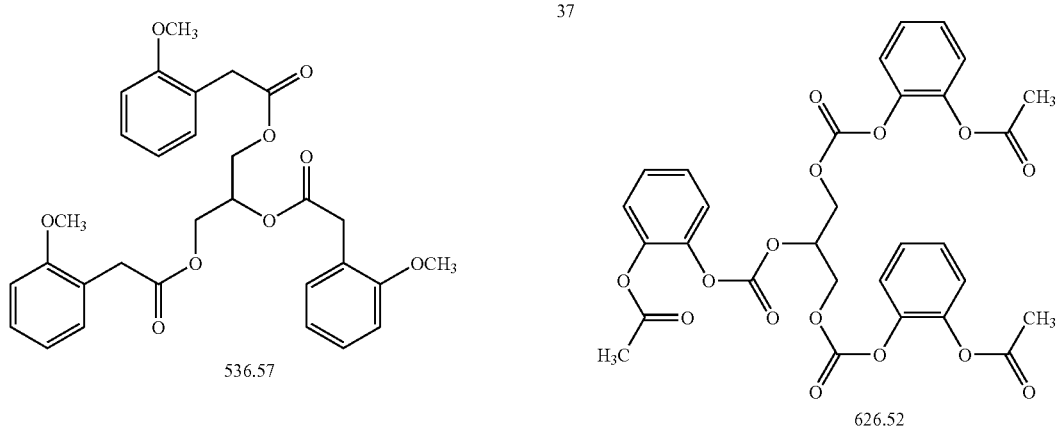
536.57
38
626.52
39
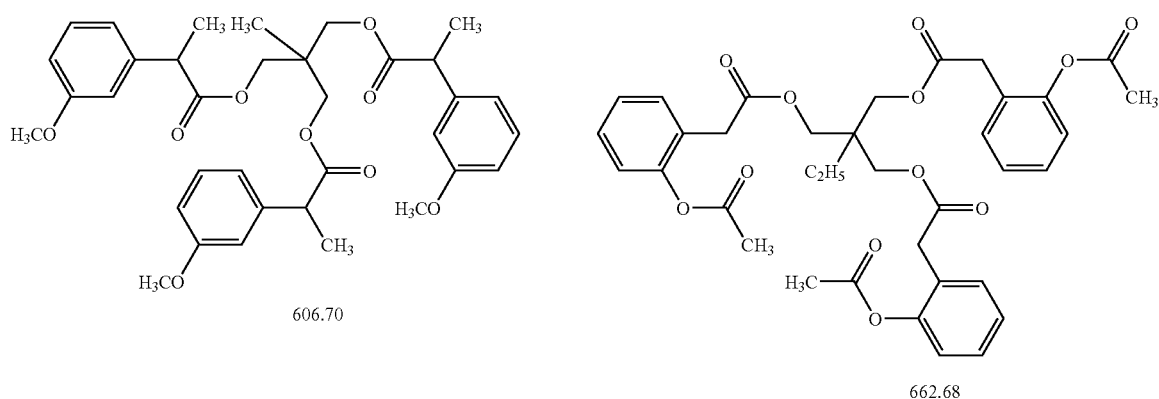
606.70
40
662.68

-continued
41
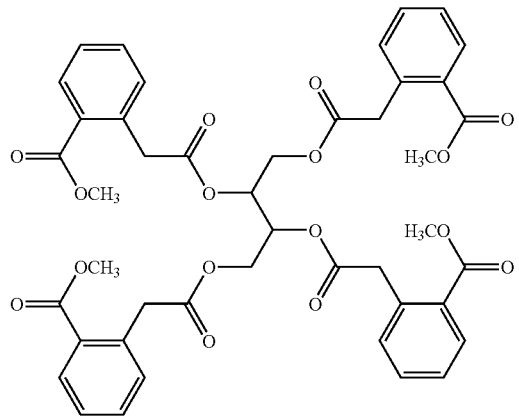
826.79
42
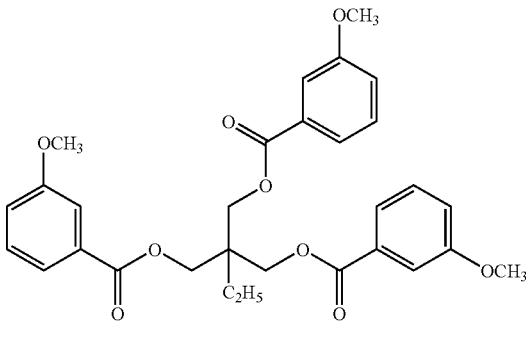
536.57
43
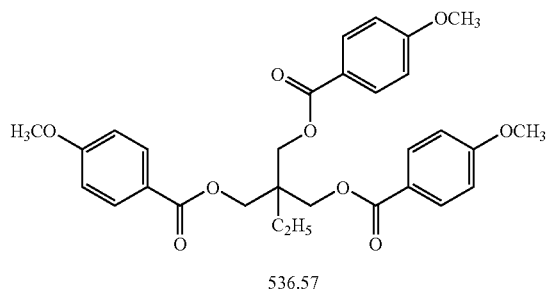
536.57
44
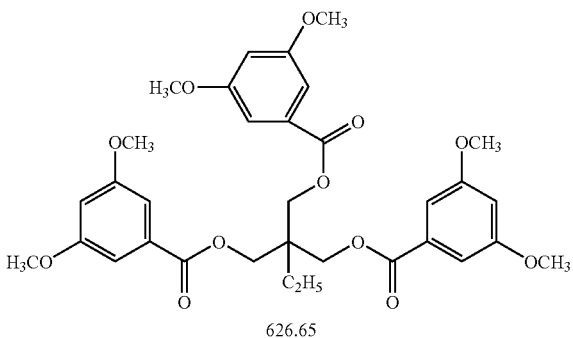
626.65
45
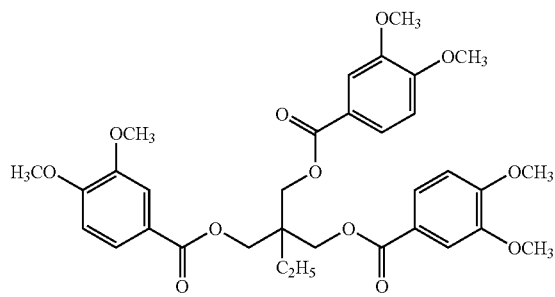
626.65
46
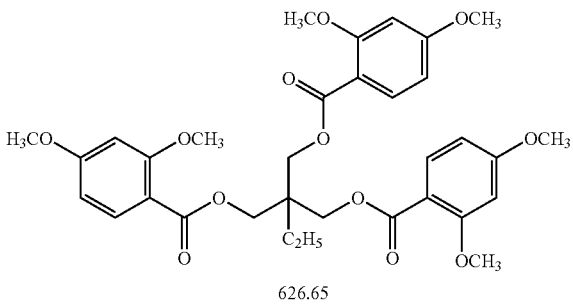
626.65
47
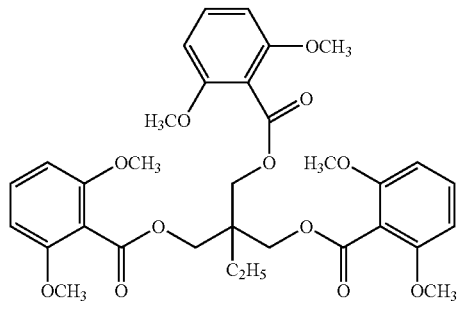
626.65
48
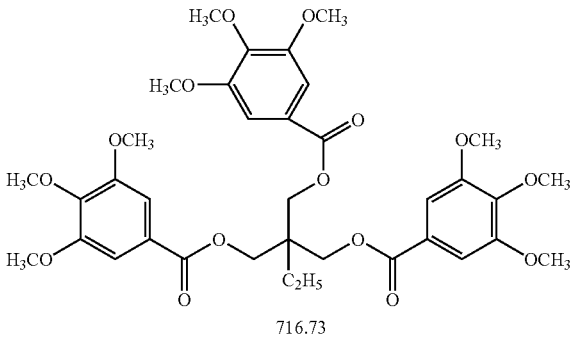
716.73

-continued
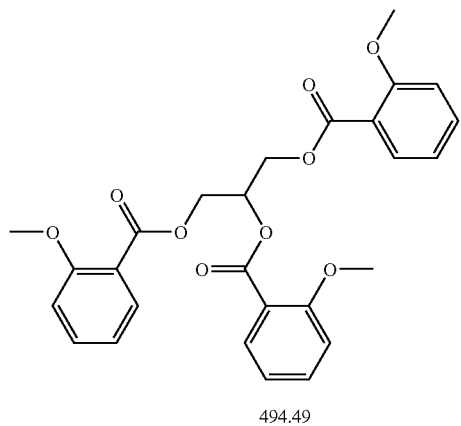
49
494.49
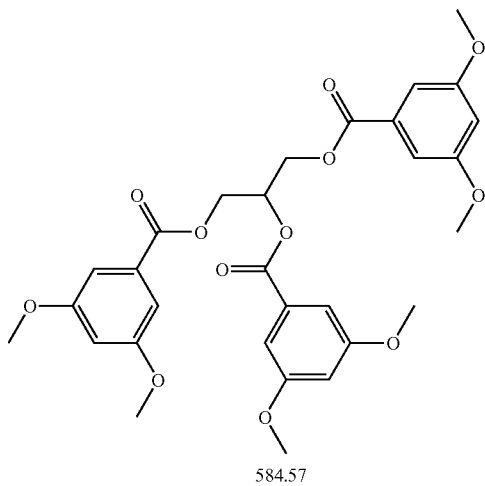
50
584.57
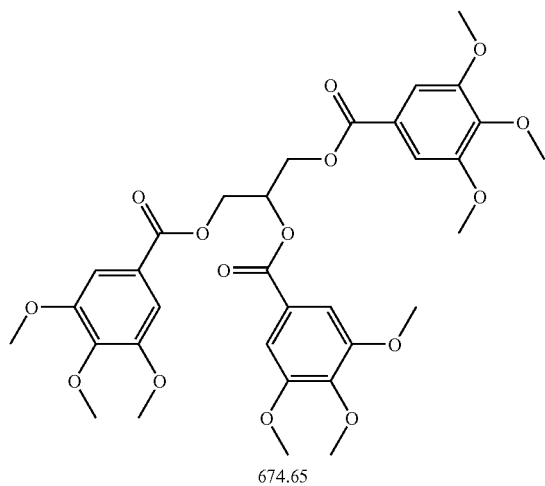
51
674.65
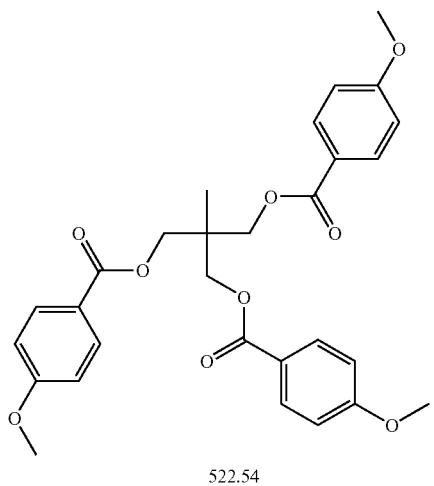
52
522.54
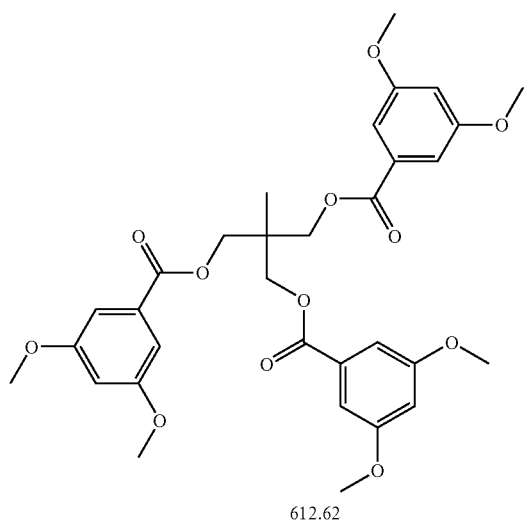
53
612.62
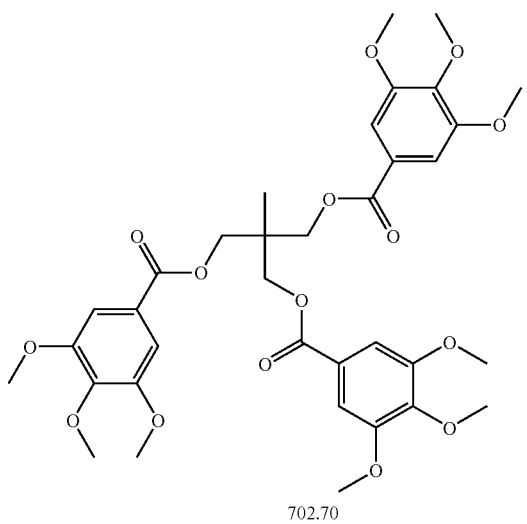
54
702.70

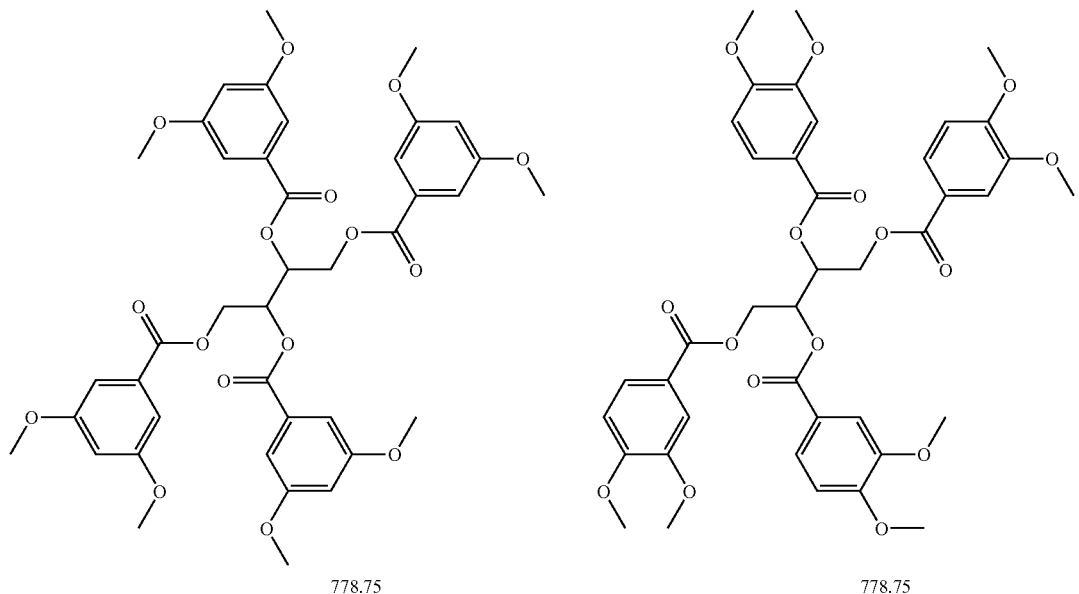
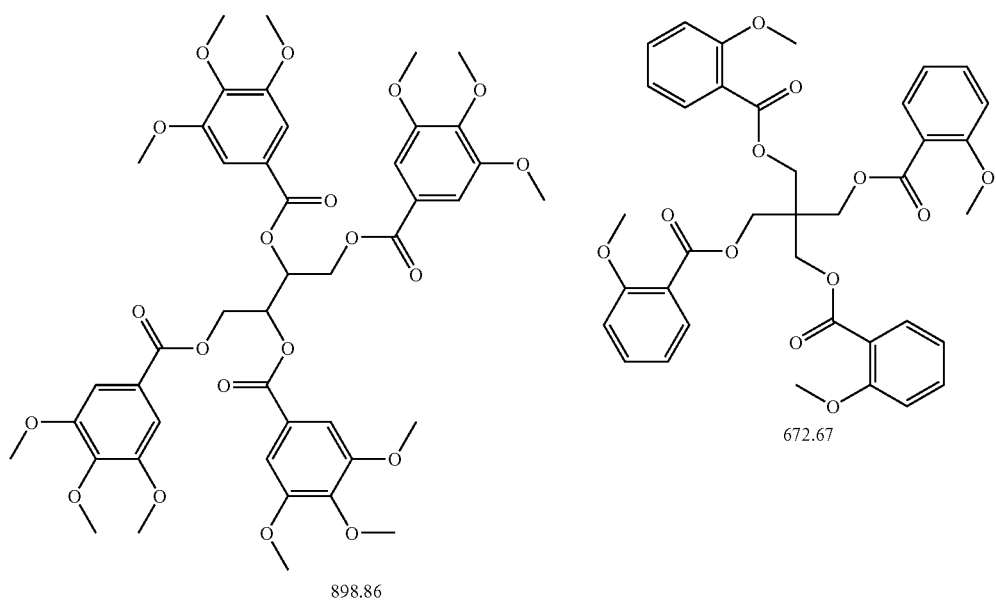

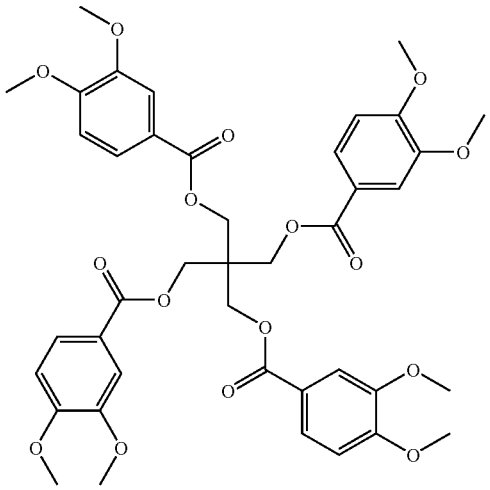

792.78

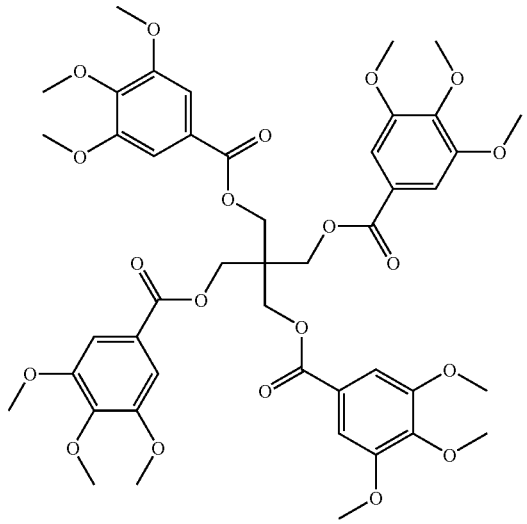

912.88

The cellulose ester film employed in the present invention incorporates in an amount of 1-25 percent by weight, as a plasticizer, at least one of the ester compounds which is produced employing the organic acid represented by above Formula (1) according to the present invention and a polyhydric alcohol having at least 3 OH groups in the molecule, but may simultaneously incorporate plasticizers other than the above.

Cellulose ester compounds composed of the organic acids represented by above Formula (1) of the plasticizers according to the present invention and polyhydric alcohol exhibit the feature of being capable of adding at a high addition rate due to its high compatibility with cellulose ester. Consequently, no bleeding-out results by a combination of other plasticizers and additives, whereby, if desired, it is possible to simultaneously and easily employ other plasticizers and additives.

Further, when other plasticizers are simultaneously employed, the ratio of the incorporated plasticizers of the present invention is preferably at least 50 percent by weight with respect to the all the plasticizers, is more preferably at least 70 percent, but is still more preferably at least 80 percent. When the plasticizers of the present invention are employed in the above range, it is possible to achieve definite effects in which it is possible to enhance the flatness of cellulose ester film during melt-casting under simultaneous use of other plasticizers.

Other plasticizers which are simultaneously employed include aliphatic carboxylic acid-polyhydric alcohol based plasticizers, unsubstituted aromatic carboxylic acid or cycloalkylcaroboxylic acid-polyhydric alcohol based plasticizers described in paragraphs 30-33 of JP-A No. 2002-12823, or dioctyl adipate, dicyclohexyl adipate, diphenyl succinate, di-2-naphthyl-1,4-cyclohexane dicarboxylate, tricyclohexyl tricarbamate, tetra-3-methylphenyltetrahydrofurane-2,3,4,5-tetracarboxylate, tetrabutyl-1,2,3,4-cyclopentane teracarboxylate, triphenyl-1,3,5-cyclohexyl tricarboxylate, triphenylbenzene-1,3,5-etracarboxylate, multivalent carboxylates such as phthalic acid based plasticizers (for example, diethyl phthalate, dimethoxyethyl phthalate, dimethyl phthalate, dioctyl phthalate, dibutyl phthalate, di-2-ethylhexyl phthalate, dioctyl phthalate, dicyclohexyl phthalate, dicyclohexyl terephthalate, methylphthalyl methyl glycolate, ethylphthalyl ethyl glycolate, propylphthalyl propyl glycolate, and butylphthalyl butyl glycolate), citric acid based plasticizers (acetyltrimethyl citrate, acetyltriethyl citrate, and acetylbutyl citrate), phosphoric acid ester based plasticizers such as triphenyl phosphate biphenyl diphenyl phosphate, butylenebis(diethyl phosphate), ethylenebis(diphenyl phosphate), phenylenebis(dibutyl phosphate), phenylenebis (diphenyl phosphate) (ADEKASTAB PFR, produced by Asahi Denka Kogyo K.K.), phenylenebis(dixylenyl phosphate) (ADEKASTAB FP500, produced by Asahi Denka Kogyo K.K.), bisphenol A diphenyl phosphate (ADEKASTAB FP600, produced by Asahi Denka Kogyo K.K.), and polyether based plasticizers such as the polymer polyesters described, for example, in paragraphs 49-56 of JP-A No. 2002-22956. Of these, as noted above, the use of phosphoric acid ester based plasticizers during melt-casting tends to result in undesired coloration. Consequently, it is preferable to employ phthalic acid ester based plasticizers, multivalent carboxylic acid ester based plasticizers, citric acid ester based plasticizers, polyester based plasticizers, and polyether based plasticizers.

Further, coloration of the cellulose ester film of the present invention results in adverse optical effects. Consequently, the degree of yellow (Yellow Index YI) is preferably at most 3.0, but is more preferably at most 1.0. It is possible to determine the Yellow Index value based on JIS K 7103.

(Cellulose Ester)

The cellulose ester employed in the present invention will now be detailed.

The cellulose ester film of the present invention is produced employing a melt-casting method. The melt-casting method makes it possible to significantly decrease the used amount of organic solvents during film production, whereby it is possible to produce films which are friendlier to the environment compared to the conventional solution-casting method which employs a large amount of organic solvents.

"Melt-casting", as described in the present invention, refers to a method in which without substantially using solvents, cellulose ester is heat-melted to the temperature to result in fluidity and casting is performed employing the resulting melt, via, for example, a method in which fluid cellulose ester is extruded from a die to result in casting. Solvents may be employed during some of the processes to prepare melted cellulose ester, but in the melt-casting process which results in film molding, the molding is performed with substantially no solvents.

Cellulose esters which constitute optical film are not particularly limited as long as they enable melt-casting, and for example, aromatic carboxylic acid esters are employed. However, in view of characteristics of film capable of achieving specified optical characteristics, it is preferable to use lower fatty acid esters of cellulose. The lower fatty acids in the lower fatty acid esters of cellulose in the present invention refer to fatty acids having at most 5 carbon atoms and examples of preferred ones include lower fatty acid esters such as cellulose acetate, cellulose propionate, cellulose butyrate, or cellulose pivarate. Cellulose esters substituted with fatty acids having at least 6 carbon atoms exhibit desired melt-casting properties. However, the resulting film exhibits insufficient dynamic characteristics, and it is difficult to use them as an optical film. In order to cope with both dynamic characteristics and melt-casting properties, employed may be mixed fatty acid esters such as cellulose acetate propionate or cellulose acetate propionate. Incidentally, the decomposition temperature of triacetyl cellulose, which is the cellulose ester commonly employed in the solution-casting, is higher than its melting temperature, whereby it is not possible to apply it to melt-casting.

Consequently, the most preferable lower fatty acid esters of cellulose are those which have an acyl group having 2-4 carbon atoms as a substituent, and satisfy following Formulas (2) and (3).

$$2.5 \leq X+Y \leq 2.9 \quad \text{Formula (2)}$$

$$0.1 \leq Y \leq 2.0 \quad \text{Formula (3)}$$

wherein X represents the degree of substitution employing acetic acid, namely the degree of substitution of an acetyl group, while Y represents the degree of substitution employing an organic acid having 3-5 carbon atoms, namely the degree of substitution employing an acyl group such as a propionyl group or a butyryl group.

Of these, cellulose acetate propionate is particularly preferably employed. Of them, it is preferable to use cellulose esters satisfying the following formulas.

$$1.0 \leq X \leq 2.5, \text{ and } 0.5 \leq Y \leq 1.5$$

The portion which is not substituted with an acyl group is present as a hydroxyl group. It is possible to synthesize the above cellulose esters employing methods known in the art.

The ratio of weight average molecular weight, Mw/number average molecular weight Mn, of cellulose esters employed in the present invention is commonly 1.0-5.5, is preferably 1.4-5.0, but is most preferably 2.0-3.0. Further, Mw of the used cellulose esters is commonly 100,000-500.000 but is preferably 200,000-400,000.

It is possible to determine the average molecular weight and molecular weight distribution of cellulose esters employing the methods known in the art which employ high speed liquid chromatography.

Measurement conditions for the above are as follows.
Solvent: methylene chlorine
Column: SHODEX K806, K805, and K803 (produced by Showa Denko K.K., these columns were used upon being connected)
Column temperature: 25° C.
Sample concentration: 0.1 percent by weight
Detector: RI Model 504 (produced by GL Science Co.)
Pump: L6000 (produced by Hitachi, Ltd.)
Flow rate: 1.0 ml/minute
Calibration curve: The used calibration curve was prepared employing 13 samples of Standard Polystyrene STK, polystyrene (produced by Tosoh Corp.) of 500-1,000,000 Mw. It is preferable that the above 13 samples are selected to result in approximately equal intervals.

Raw cellulose materials of the cellulose esters employed in the present invention may be either wood pulp or cotton linter. Wood pulp may be made from either conifers or broad-leaved trees, but coniferous pulp is more preferred. However, in view of peeling properties during casting, cotton linters are preferably employed. Celluloses esters prepared employing these materials may be employed individually or in appropriate combinations.

For example, the following ratios are possible: cellulose ester derived from cotton linter:cellulose ester derived from wood pulp (conifers):cellulose ester derived from wood pulp (broad-leaved trees) is 100:0:0, 90:10:0, 85:15:0, 50:50:0, 20:80:0, 10:90:0, 0:100:0, 0:0:100, 80:10:10, 85:0:15, and 40:30:30.

It is possible to prepare cellulose esters by replacing the hydroxyl group of cellulose raw materials with an acetyl group, an propionyl group, and/or a butyl group, employing acetic anhydride, propionic anhydride, and/or butyric anhydride based on conventional methods. Synthesis methods of such cellulose esters are not particularly limited, and it is possible to synthesize them with reference to, for example, JP-A No. 10-45804 or JP-A (under PCT Application) No. 6-501040.

It is possible to determine the degree of substitution of the acetyl group, propionyl group, and butyl group based on ASTM-D817-96. The total amount of the residual acid (e.g. acetic acid) is preferably not more than 1000 ppm.

Further, cellulose esters are industrially synthesized employing sulfuric acid as a catalyst, however the above sulfuric acid is not easily completely removed. The residual sulfuric acid undergoes various types of decomposition reactions to result in adverse effects to product quality of the resulting cellulose ester films. Consequently, it is desirable to control the residual sulfuric acid in the cellulose esters employed in the present invention within the range of 0.1-40 ppm in terms of sulfur element. It is assumed that these acids are incorporated in the form of salts. It is not preferable that the content of the residual sulfuric acid exceeds 40 ppm, because adhering materials on die lips increase during heat melting. Further, it is preferable that the content is relatively small. However, it is not preferable that content is at most 0.1, because achieving at most 0.1 results in excessively large load for the washing process of cellulose resins and further on the contrary, breakage tends to occur during or after heat stretching. It is assumed that an increase in washing frequency adversely affects the resins, but the reasons for this are not well understood. The content of the residual sulfuric acid is more preferably in the range of 0.1-30 ppm. It is also possible to determine the content of the residual sulfuric acid based on ASTM-D817-96.

By further sufficiently washing synthesized cellulose compared to the case in which the solution-casting method is employed, it is possible to achieve the desired content of residual sulfuric acid to be within the above range. Thus, during production of film employing the melt-casting method, adhesion to the lip portions is reduced to produce films of excellent flatness, whereby it is possible to produce films which exhibit excellent dimensional stability, mechanical strength, transparency, and water vapor transmitting resistance, as well as the desired Rt and Ro values described below.

Further, the limiting viscosity of cellulose resins is preferably 1.5-1.75 g/cm$^3$, but is more preferably 1.53-1.63.

Still further, it is preferable that when the cellulose esters employed in the present invention are converted to a film, the resulting film produces minimal foreign matter bright spots. "Foreign matter bright spots" refers to the following type of spots. A cellulose ester film is placed between two polarizing plates arranged at right angles (crossed Nicols) and light is exposed on one side while the other side is viewed. When foreign matter is present, light leaks through the film and a phenomenon occurs in which foreign matter particles are seen as bright spots. During this operation, the polarizing plate, which is employed for evaluation, is composed of a protective film without any foreign matter bright spots, whereby a glass plate is preferably employed to protect polarizers. It is assumed that one of the causes of foreign matter bright spots is the presence of cellulose which has undergone no acetylation or only a low degree of acetylation. It is necessary to employ cellulose esters (or employing cellulose esters exhibiting a degree of uniform substitution). Further, it is possible to remove foreign matter bright spots in such a manner that melted cellulose esters are filtered, or during either the latter half of the synthesis process of the cellulose esters, or during the process to form precipitates, a solution is temporarily prepared and is filtered via a filtration process. Since melted resins exhibit high viscosity, the latter method is more efficient.

It is likely that as the film thickness decreases, the number of foreign matter bright spots per unit area decreases, and similarly, as the content of cellulose ester incorporated in films decreases, foreign matter bright spots decreases. The number of at least 0.01 mm foreign matter bright spots is preferably at most 200, is more preferably at most 100, is still more preferably at most 50, is still more preferably at most 30, is yet more preferably at most 10, but is most preferably of course zero.

In cases in which bright spot foreign matter is removed via melt-filtration, it is preferable to filter the melted composition composed of cellulose esters, plasticizers, degradation resistant agents, and antioxidants, rather than to filter melted individual cellulose ester, whereby bright spot foreign matter is efficiently removed. Of course, bright spot foreign matter may be reduced in such a manner that during synthesis of cellulose ester, the resulting cellulose ester is dissolved in solvents and then filtered. It is possible to filter compositions which appropriately incorporate UV absorbers and other additives. The viscosity of the melt, incorporating cellulose esters, which is to be filtered, is preferably at most 10,000 P, is more preferably at most 5,000 P, is still more preferably at most 1,000 P, but is most preferably at most 500 P. Preferably employed as filters are those known in the art, such as glass fibers, cellulose fibers, paper filters, or fluorine resins such as tetrafluoroethylene. However, ceramic and metal filters are particularly preferably employed. The absolute filtrations accuracy of employed filters is preferably at most 50 µm, is more preferably at most 30 µm, is still more preferably at most 10 µm, but is most preferably at most 5 µm. It is possible to employ them in suitable combinations. Employed as a filter, may be either a surface type or a depth type. The depth type is more preferably employed since it is relatively more free from clogging.

In another embodiment, employed as raw cellulose ester materials may be those which are dissolved in solvents at least ounce, and then dried to remove the solvents. In this case, cellulose ester is dissolved in solvents together with at least one of a plasticizer, an UV absorber, a degradation resistant agent, an antioxidant, and a matting agent. Thereafter, the mixture is dried and then used as a cellulose ester composition. Employed as solvents may be good solvents, such as methylene chloride, methyl acetate, dioxolan, which are employed in the solution-casting method, while poor solvents such as methanol, ethanol, or butanol may also be simultaneously employed. In the dissolving process, cooling may be performed to −20° C. or lower, or heated to 80° C. or higher. By employing such cellulose ester, it is possible to uniformly mix each of the additives in a melted state and, it is occasionally possible to make the resulting optical characteristic very uniform.

The optical film of the present invention may be one which is formed by suitably blending polymer components other than cellulose esters. Polymers to be blended are preferably those which are highly compatible with cellulose esters. When converted to a film, the resulting transmittance is preferably at least 80 percent, is more preferable at least 90 percent, but is still more preferably 92 percents.

(Other Additives)

Other than cellulose esters and plasticizers, in the cellulose ester film of the present invention incorporated may be various functional additives such as stabilizers, lubricants, matting agents, fillers, inorganic polymers, organic polymers, dyes, pigments, phosphors, UV absorbers, infrared ray absorbers, diachronic dyes, refractive index controlling agents, retardation controlling agents, gas transmission retarding agents, antimicrobial agents, electric conductivity enhancing agents, biodegradability enhancing agents, gelatin inhibitors, or thickeners.

The cellulose esters of the present invention are melt-cast at a relatively high temperature such as 200-250° C., whereby in the process, decomposition and degradation of cellulose esters tend to occur compared to conventional solution-casting film production. Consequently, it is preferable that of the above additives, especially stabilizers are incorporated into film forming materials.

Examples of stabilizers include, but are not limited to, antioxidants, acid scavengers, hindered amine light stabilizers, UV absorbers, peroxide decomposing agents, radical scavengers, and metal inactivating agents. These are described in JP-A Nos. 3-199201, 5-1907073, 5-194789, 5-371471, and 6-107854. It is preferable that at least one which is selected from those is incorporated in the film forming materials.

Further, when the cellulose ester film of the present invention is employed as a polarizer protecting film or a retardation film, the polarizer is easily degraded by ultraviolet radiation. Consequently, it is preferable that UV absorbers are incorporated into at least the light incident side of the polarizer.

Further, when the cellulose ester film of the present invention is employed as a retardation film, it is possible to incorporate additives to control the retardation. Employed as additives to control retardation may be the retardation controlling agents described in European Patent No. 911,656A2.

Still further, in order to control the viscosity during heatmelt and to regulate physical film properties after film treatment, it is possible to add organic or inorganic polymers.

During addition of these additives to cellulose ester resins, the total amount including the above additives is 1-30 percent by weight with respect to the weight of cellulose ester resins. When the amount is at most one percent by weight, meltcasting properties are degraded, while when it exceeds 30 percent by weight, it is not possible to achieve desired dynamic characteristics nor desired storage stability.

(Antioxidants)

Since decomposition of cellulose esters is accelerated not only by heat but also by oxygen at the high temperature at which melt-casting is performed, it is preferable that antioxidants are incorporated as a stabilizer into the optical film of the present invention. Antioxidants which are used as a useful antioxidant in the present invention are not particularly limited as long as they are compounds which retard degradation of melt-molded materials via the presence of oxygen. Useful antioxidants include hindered phenol based antioxidants, hindered amine based antioxidants, phosphorous based antioxidants, sulfur based antioxidants, heat resistant process stabilizing agents, and oxygen scavengers. Of these, particularly preferred are hindered phenol based antioxidants, hindered amine based antioxidants and phosphorous based antioxidants. By blending these antioxidants, it is possible to minimize coloration and strength degradation of molded products due to heat, as well as thermal oxidation degradation during melt molding. These antioxidants may be employed individually or in combinations of at least two types.

Of the above antioxidants, preferred are hindered phenol based antioxidants. The hindered phenol based antioxidants are prior art compounds, which are described, for example, in column 12-14 of U.S. Pat. No. 4,839,405, including 2,6-dialkyl phenol derivatives. Of such compounds, included as preferable compounds are those represented by Formula (4) below.

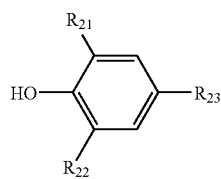

Formula (4)

wherein $R_{21}$, $R_{22}$ and $R_{23}$ each represent a substituted or unsubstituted alkyl substituent. Specific examples of hindered phenol compounds include n-octadecyl 3-,5-di-t-butyl-4-hydroxyphenyl)-propionate, n-octadecyl 3-(3,5-di-t-butyl-4-hydroxybenzoate, n-hexyl 3,5-di-t-butyl-4-hydroxyphenylbenzoate, n-dodecyl 3,5-di-t-butyl-4-hydroxyphenyl benzoate, neo-dodecyl 3,5-di-t-butyl-4-hydroxyphenyl)propionate, dodecyl β(3,5-di-t-butyl-4-hydroxyphenyl)propionate, ethyl α-(4-hydroxy-3,5-di-t-butylphenyl)isobutyrate, octadecyl α-(4-hydroxy-3,5-di-t-butylphenyl)isobutyrate, octadecyl α-(4-hydroxy-3,5-di-t-butyl-4-hydroxyphenyl)propionate, 2-n-octylthio) ethyl 3,5-di-t-butyl-4-hydroxy-benzoate, 2-n-octylthio) ethyl 3,5-di-butyl-4-hydroxy-phenyl acetate, 2-(n-octadecylthio)ethyl 3,5-di-t-butyl-4-hydroxyphenyl acetate, 2-(n-octadecylthio) ethyl 3,5-di-t-butyl-4-hydroxy-benzoate, 2-(2-hydroxyethylthio)ethyl 3,5-di-t-butyl-4-hydroxybenzoate, diethylglycolbis-(3,5-di-t-butyl-4-hydroxyphenyl) propionate, 2-(n-octadecythio)ethyl 3-(3,5-di-t-butyl-4-hydroxyphenyl) propionate, stearylamido N,N-bis-[ethylene 3-(3,5-di-t-butyl-4-hydroxyphenyl)propionate], n-butylimino N,N-bis-[ethylene 3-(3,5-di-t-butyl-4-hydroxyphenyl)propionate], 2-(2-stearoyloxyethylthio)ethyl 3,5-di-t-butyl-4-hydroxybenzoate, 2-(2-stearoyloxyethylthio)ethyl 7-(3-methyl-5-t-butyl-4-hydroxyphenyl) heptanoate, 1,2-propyleneflycolbis-[3-(3,5-di-t-butyl-4-hydroxyphenyl)propionate], ethyleneglycolbis-[3-(3,5-di-t-butyl-4-hydroxyphenyl) propionate], neopentylglycolbis-[3-(3,5-di-t-butyl-4-hydroxyphenyl) propionate], ethyleneglyxolbis-(3,5-di-t-butyl-4-hydroxyphenyl acetate), glycerin-1-n-octadecanoate-2,3-bis-(3,5-di-t-butyl-4-hydoxyphenyl acetate), pentaerythritol-tetrakis-[3-(3',5'-di-t-butyl-4'-hydoxyphenyl) propionate], 1,1,1-trimethylolethane-tris-[3-(3,5-di-t-butyl-4-hydroxyphenyl) propionate], sorbitolhexa-[3-(3,5-di-t-butyl-4-hydroxyphenyl) propionate], 2-hydroxyethyl 7-(3-methyl-5-t-butyl-4-hydroxyphenyl) propionate, 2-stearoyloxyethyl 7-(3-methyl-5-t-butyl-4-hydroxyphenyl) heptanoate, 1,6-n-hexanediol-bis[(3',5'-di-t-butyl-4-hydroxyphenyl) was propionate], and pentaerythritol-tetrakis(3,5-di-t-butyl-4-hydroxyhydrocinnamate). The above type hindered phenol compounds are commercially available under trade names such as "IRGANOX 1076" or "IRGANOX 1010" from Ciba Specialty Chemicals.

The phosphorous based antioxidants are known compounds and preferred examples are shown in Formula (1) of JP-A No. 2002-138188. An example of compound available in the market is SUMILIZER GP (produced by Sumitomo Chemical Co. Ltd.)

The addition amount of antioxidants is preferably 0.1-10 percent by weight, is more preferably 0.2-5 percent by weight, but is still more preferably 0.5-2 percent by weight. These may be employed in combinations of at least two types.

(Acid Scavengers)

At the relatively high temperature at which melt-casting is performed, decomposition of cellulose esters is also accelerated by the presence of acids, whereby it is preferable that the optical film of the present invention incorporates acid scavengers as a stabilizer. Acid scavengers in the present invention may be employed without any limitation, as long as they are compounds which react with acids to inactivate them. Of such compounds, preferred are compounds having an epoxy group, as described in U.S. Pat. No. 4,137,201. Epoxy compounds as such an acid scavenger are known in this technical field, and include diglycidyl ethers of various polyglycols, especially, polyglycols which are derived by condensation of ethylene oxides in an amount of about 8-about 40 mol per mol of polyglycol, metal epoxy compounds (for example, those which have conventionally been employed together with vinyl chloride polymer compositions in vinyl chloride polymer compositions), epoxidized ether condensation products, diglycidyl ethers (namely, 4,4'-dihydroxydiphenyldimethylmethane) of bisphenol A, epoxidized unsaturated fatty acid esters (particularly, alkyl esters (for example, butyl epoxystearate) having about 2-about 4 carbon atoms of fat acids having 2-22 carbon atoms), epoxidized plant oils which can be represented and exemplified by compositions of various epoxidized long chain fatty acid triglycerides (for example, epoxidized soybean oil and epoxidized linseed oil and other unsaturated natural oils (these are occasionally called epoxidized natural glycerides or unsaturated fatty acid and these fatty acid have 12-22 carbon atoms). Further, preferably employed as commercially available epoxy group incorporating epoxide resinous compounds may be EPSON 815C and other epoxidized ether, oligomer condensation products represented by Formula (5).

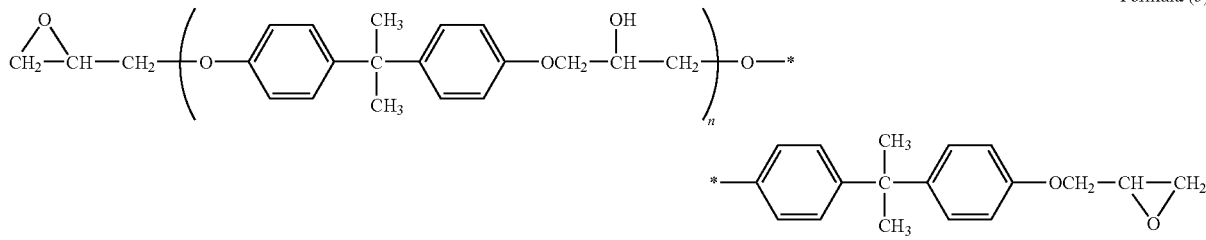

Formula (5)

wherein n represent an integer of 0-12. Other usable acid scavengers include those described in paragraphs 87-105 of JP-A No. 5-194788. The added amount of acid scavengers is preferably 0.1-10 percent by weight, but is more preferably 0.5-2 percent by weight. These may be employed in combinations of at least two types.

Further, acid scavengers may also be called acid catchers, but in the present invention, it is possible to use them regardless name.

(UV Absorbers)

In view of minimizing degradation of polarizers and display units due to ultraviolet radiation, UV absorbers, which absorb ultraviolet radiation of a wavelength of at most 370 nm, are preferred, while in view of liquid crystal display properties, UV absorbers, which minimize absorption of visible light of a wavelength of at least 400 nm, are preferred. Examples of UV absorbers employed in the present invention include oxybenzophenone based compounds, benzotriazole based compounds, salicylic acid ester based compounds, benzophenone based compounds, cyanoacrylate based compounds, nickel complex based compounds, and triazine based compounds. Of these, preferred are benzophenone based compounds, as well as benzotriazole based compounds and triazine compounds which result in minimal coloration. Further, employed may be UV absorbers described in JP-A Nos. 10-182621 and 8-337574, as well as polymer UV absorbers described in JP-A Nos. 6-148430 and 2003-113317.

Specific examples of benzotriazole UV absorbers include, but are not limited to, 2-(2'-hydroxy-5'-methylphenyl)benzotriazole, 2-(2'-hydroxy-3',5'-di-tert-butylphenyl)benzotriazole, 2-(2'-hydroxy-3'-tert-butyl-5'-methylphenyl)benzotriazole, 2-(2'-hydroxy-3',5'-di-tert-butylphenyl)-5-chlorobenzotriazole, 2-(2'-hydroxy-3'-(3",4",5",6"-tetrahydrophthalimidomethyl)-5'-methylphenyl) benzotriazole, 2,2-methylenebis(4-(1,1,3,3-tetramethylbutyl)-6-(2H-benzotriazole-2-yl)phenol), 2-(2'-hydroxy-3'-tert-butyl-5'-methylphenyl)-5-chlorobenzotriazole, and 2-(2H-benzotriazole-2-yl)-6-(straight chain and branched chain dodecyl)-4-methylphenol, as well as a mixture of octyl-3-[3-tert-butyl-4-hydroxy-5-(chloro-2H-benzotriazole-2-yl)phenyl] propionate and 2-ethylhexyl-3-[3-tert-butyl-4-hydroxy-5-(5-chloro-2H-benzotriazole-2-yl)phenyl] propionate.

Listed as such commercially available products are TINUVIN 171, TINUVIN 234, TINUVIN 360, all produced by Ciba Specialty Chemicals Co.) and LA 31 (produced by Asahidenka. CO. Ltd.).

Specific examples of benzophenone compounds include, but are not limited to, 2,4-dihydroxybenzophenone, 2,2'-dihydroxy-4-methoxybenzopheneone, 2-hydroxy-4-methoxy-5-sulfobenzophenone, and bis(2-methoxy-4-hydroxy-5-benzoylphenylmethane).

In the present invention, the added amount of UV absorbers is preferably 0.1-5 percent by weight, is more preferably 0.2-3 percent by weight, but is still more preferably 0.5-2 percent by weight. These may be employed in combinations. Further, these benzotriazole structure and benzophenone structure may be hung to a portion of polymers, or regularly to polymers and may further be incorporated into a part of the molecular structure of other additives such as plasticizers, antioxidants, or acid scavengers.

(Hindered Amine Compounds)

Other than above antioxidants, acid scavengers, and UV absorbers, listed as additives which enable retardation of decomposition of cellulose esters, via heat and light, are hindered amine compounds, which may be incorporated into the cellulose ester film, if desired.

Hindered amine compounds (HALS) employed in the present invention include 2,2,6,6-tetraalkylpiperidine compounds, or acid addition salts thereof or metal complexes thereof, as described, for example, in columns 5-11 of U.S. Pat. No. 4,619,956 as well as columns 3-5 of U.S. Pat. No. 4,839,405. The above compounds are included in the compounds represented by Formula (5) below.

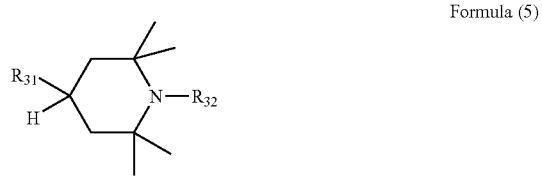

Formula (5)

wherein $R_{31}$ and $R_{32}$ each represent H or a substituent. Specific examples of hindered amine compounds include 4-hydroxy-2,2,6,6-tetramethylpiperidine, 1-allyl-4-hydroxy-2,2,6,6-tetramethylpiperidine, 1-benzyl-4-hydroxy-2,2,6,6-tetramethylpiperidine, 1-(4-t-butyl-2-butenyl)-4-hydroxy-2,2,6,6-tetramethylpiperidine, 4-stearoyloxy-2,2,6,6-tetramethylpiperidine, 1-ethyl-4-salycloyloxy-2,2,6,6-tetramethylpiperidine, 4-methacroyloxy-1,2,2,6,6-pentamethylpiperidine, 1,2,2,6,6-pentamethylpiperidine-4-yl-β(3,5-di-t-butyl-4-hydroxyphenyl)-propionate, 1-benzyl-2,2,6,6-tetramethyl-4-pyperidinyl maleinate, (di-2,2,6,6-tetramethylpiperidine-4-yl)-adipate, 6,6-tetramethylpieridine-4-yl)-sebacate, (di-1,2,3,6-tetramethyl-2,6-diethyl-piperidine-4-yl)-sebacate, (di-1-allyl-2,2,6,6-tetramethylpiperidine-4-yl)-phthalate, 1-acetyl-2,2,6,6-tetramethylpiperidine-4-yl-acetate, trimellitic acid-tri-(2,2,6,6-tetramethylpiperidine-4-yl) ester, 1-acryloyl-4-benzyloxy-2,2,6,6-tetramethylpiperidine, dibutyl-malonic acid-di-(1,2,2,6,6-pentamethyl-piperidine-4-yl)-ester, dibenzyl-malonic acid-di-(1,2,3,6-tetramethyl-2,6-dethyl -piperidine-4-yl)-ester, dimethyl-bis-(2,2,6,6-tetramethylpiperidine-4-oxy)-silane, tris-(1-propyl-2,2,6,6-tetramethylpiperidine-4-yl)-phosphite, tris-(1-propyl-2,2,6,6-tetramethylpiperidine-4-yl)-phosphate, N,N'-bis-(2,2,6,6-tetramethylpiperidine-4-yl)-hexamethylene-1,6-diamine, N,N'-bis-(2,2,6,6-tetramethylpiperidine-4-yl)-hexamethylene-1,6-diacetamide, 1-acetyl-4-(N-cyclohexylacetamido)-2,2,6,6-tetramethyl-piperidine, 4-benzylamino-2,2,6,6-tetramethylpiperidine, N,N'-bis-(2,2,6,6-tetramethylpiperidone-4-yl)-N,N'-dibutyl-adipamide, N'-bis-(2,2,6,6-tetramethylpiperidine-4-yl)-N,N'dicyclohexyl-(2-hydroxypropylene), N,N'-bis-(2,2,6,6-tetramethylpiperidine-4-yl)-p-xylene-diamine, 4-(bis-2-hydroxyethyl)-amino-1,2,2,6,6-pentamethylpiperidine, 4-methacrylamido-1,2,2,6,6-pentaethylpiperidine, and α-cyano-β-methyl-β-[N-(2,2,6,6-tetramethylpiperidine-4-yl)]-amino-acrylate ester. The examples of preferred hindered amine compounds include, but are not limited to, HALS-1 and HALS-2 below.

is preferable that these minute particles are subjected to a surface treatment, since it is possible to lower the film haze.

It is preferable to carry out the above surface treatment employing halosilanes, alkoxysilanes, silazane, or siloxane. As the average diameter of minute particles increases, slipping effects are enhanced. On the other hand, as it decreases, the resulting transparency increases. Further, the average diameter of the primary particles of the minute particles is customarily in the range of 0.01-1.0 μm, is preferably 5-50 nm, but is more preferably 7-14 nm. These minute particles are preferably employed to result in unevenness of 0.01-1.0 μm of the cellulose ester film surface.

Listed as minute silicon dioxide particles are AEROSIL 200, 200V, 300, R972, R974, R202, R812, OX50, and TT600, all produced by Nihon Aerosil Corp. Of these, preferred are AEROSIL 200V, R972, R972V, R974, R202, and R812.

When two types of the above are employed in combination, they may be mixed at an optional ratio and then employed. It

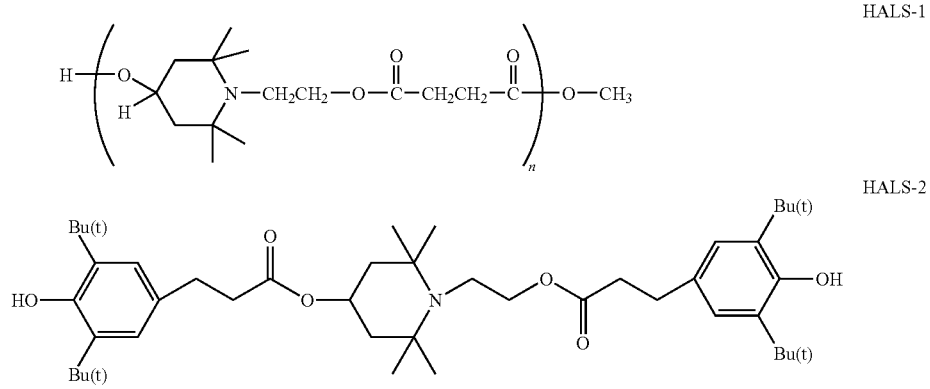

HALS-1

HALS-2

It is preferable that at least one of the above compounds is incorporated. The content is preferably 0.01-5 percent by weight with respect to the weight of the cellulose ester resins, is more preferably 0.1-3 percent by weight, but is still more preferably 0.1-2 percent by weight.

When the content of the above compounds is less than the above lower limit, cellulose ester resins tend to undergo thermal decomposition, while when it is more than the above upper limit, in view of compatibility to resins, transparency required for the polarizing plate protecting film is insufficient and the resulting film becomes fragile. Consequently, neither case is not preferred.

(Matting Agents)

In order to provide aimed slip properties, as well as to optical and mechanical functions, it is possible to incorporate matting agents into the cellulose ester film of the present invention. Listed as such matting agents are minute particles of inorganic or organic compounds.

Preferably employed matting agents are spherical, rod-shaped, acicular, layered and tabular. Listed as matting agents are, for example, metal oxides such as silicon dioxide, titanium dioxide, aluminum oxide, zirconium oxide, calcium carbonate, kaolin, talc, calcined calcium silicate, hydrated calcium silicate, aluminum silicate, magnesium silicate, or calcium phosphate; minute inorganic particles composed of phosphoric acid salts, silicic acid salts, or carbonic acid salts; and minute crosslinking polymer particles. Of these, silicon dioxide is preferred due to a resulting decrease in film haze. It is possible to use minute particles which differ in their average particle diameter and materials, such as AEROSIL 200V and R972V at a ratio of 0.1:99.9, in terms of weight ratio.

These matting agents are added employing a method in which they are kneaded. Another method is that matting agents are previously dispersed and the resulting dispersion is blended with cellulose ester and/or plasticizers and/or UV absorbers. Thereafter, the resulting mixture is dispersed and subsequently solids are obtained by vaporizing the solvents or by performing precipitation. The resulting product is preferably employed in the production process of a cellulose ester melt since it is possible to uniformly disperse the matting agents into cellulose resins.

It is possible to incorporate the above matting agents to improve mechanical, electrical, and optical characteristics.

As the added amount of these minute particles increases, the slipping properties of the resultant cellulose ester film are enhanced, while haze increases. The content is preferably 0.001-5 percent by weight, is more preferably 0.005-1 percent by weight, but is still more preferably 0.01-0.5 percent by weight.

The haze value of the cellulose ester film of the present invention is preferably at most 1.0 percent, but is more preferably at most 0.5 percent, since optical materials at a haze value of at least 1.0 percent result in adverse effects. It is possible to determine the haze value based on JIS K 7136.

The cellulose ester film of the present invention is formed employing a melt-casting method. A molding method in which melt-casting is performed during heat-melting without using solvents (for example, methylene chloride) employed in the solution-casting method is, specifically, classified as a melt-extrusion molding method, a press-molding method, an inflation method, an ejection molding method, a blow-molding method, or a stretching molding method. Of these, in order to produce a polarizing plate protecting film which exhibits desired mechanical strength and surface accuracy, the melt-extrusion method is superior. When the physical properties of the resulting cellulose ester film is taken into account, melt temperature are preferably in the range of 120-280° C., but is more preferably in the range of 200-250° C.

Namely, raw material cellulose esters molded into powders or pellets are subjected to hot air drying or vacuum drying, and are heat-melted together with film constituting materials to result in fluidity. Thereafter, the resulting melted mixture is extruded into a sheet through a T-die, and for example, is brought into close contact with a cooling drum or a looped belt, employing an electrostatic application method, cooling-solidified, whereby an un-stretched sheet is produced. It is preferable that the temperature of the cooling drum is maintained in the range of 90-150° C.

It is preferable that the film peeled from the cooling drum is re-heated and subjected to single step or multi-step stretching in the longitudinal direction employing a heating unit such as a infrared heater, and then cooled. During these processes, it is preferable that the film is heated preferably in the range of $(Tg-30)°$ C.-$(Tg+100)°$ C., wherein Tg represents the transition temperature, but more preferably in the range of $(Tg-20)°$ C.-$(Tg+80)°$ C. is stretched either in the moving direction (the longitudinal direction: MD) or in the transverse direction (TD). It is preferable that transverse stretching is performed in the temperature range of $(Tg-20)°$ C.-$(Tg+20)°$ C. and subsequently and the resulting film is subjected to heat fixing. It is also preferable that after the stretching process, the resulting film is subjected to a relaxation treatment.

It is possible to control the Tg of cellulose ester film depending on the type and ratio of film constituting materials. In the use of present invention, Tg is preferably at least 120° C., but is more preferably at least 135° C. The reasons for this are as follows. In cases in which the cellulose ester film of the present invention is applied to liquid crystal display units, and when the Tg of the above film is at most the above temperature, the temperature in the orientation state of molecules fixed in the film interior is adversely affected by effects of the used ambience temperature and backlight heat, and retardation values, dimensional stability, and shape tend to easily vary. On the other hand, when the Tg of the film is excessively high, it is difficult to realize production due to reaching the decomposition temperature of film constituting materials. Further, due to decomposition of materials which are employed for film casting, volatile components and coloration are occasionally result. Consequently, the Tg is preferably at most 200° C., but is more preferably at most 170° C. During this operation, film Tg is determined based on the method described in JIS K 7121.

When performing transverse stretching (transverse direction: TD), it is preferable that transverse stretching is performed in a stretching zone which is divided into at least two zones while successively increasing temperature within a range of temperature difference of 1-5° C., since thereby physical properties in the transverse direction becomes more uniform. Further, after the transverse stretching, when the resulting film is maintained in the range of at most final stretching temperature and at least Tg−40° C. for 0.01-5 minutes, it is possible to make physical properties in the transverse direction more uniform. Consequently, the above operation is preferred.

Heat fixing is carried out in the temperature range of at least the final stretching temperature to at most Tg−20° C. commonly, for 0.5-300 seconds. During this operation, it is preferable that heat fixing is carried out in a zone which is divided into at least two while successively increasing temperature in a range of temperature difference of 1-100° C.

Heat-fixed film is commonly cooled to Tg or a temperature lower than Tg, and is wound after the clip holding portions on both sides of the film are slit off. During the above treatments, it is preferable that a relaxation treatment by 0.1-10 percent is performed in the transverse and/or longitudinal direction. Further, it is preferable that gradual cooling is performed from the final heat-fixing temperature to Tg at a cooling rate of 100° C. per second or less. The means to perform cooling and the relaxation treatment are not particularly limited, and prior art methods may be employed. In view of enhancing the dimensional stability of the film, it is particularly preferable that these treatments are performed at a plurality of temperature ranges under successive cooling. "Cooling rate", as described herein, refers to the value obtained based on $(T1-T2)/t$, wherein T1 represents the final heat-fixing temperature, T2 represents the temperature after cooling, and t represents the time necessary for cooling the film from T1 to T2.

Optimal heat-fixing conditions as well as cooling and relaxation conditions differ depending on the cellulose esters which constitute the film. Consequently, these conditions may be appropriately determined to result in preferred characteristics upon measuring the physical properties of the resulting biaxially stretched film.

The stretching factor of cellulose ester films is 1.01-3.00 in both the longitudinal and transverse directions, is more preferably 1.01-2.50, but is still more preferably 1.01-2.00. By doing so, it is possible to produce a cellulose ester film which exhibits excellent optical isotropy and, simultaneously, excellent flatness. It is preferable to perform such width holding or stretching in the longitudinal direction, employing a tenter, which may be either a pin or a clip type.

Further, in the case of production of a retardation film, it is possible to produce an optically anisotropic film by stretching in such a manner that stretching factors in the longitudinal and transverse directions are allowed to differ and one stretching factor is different from the other. During the above operation, the ratio of stretching factor in the transverse direction to the longitudinal direction is preferably 1.1-2.0, but is more preferably 1.1-1.5.

In cases in which the optical film of the present invention is employed as a polarizing plate protecting film, the thickness of the above protective film is preferably 10-500 μm, is more preferably 10-100 μm, is still more preferably 20-80 μm, but is most preferably 30-60 μm. When the thickness of the cellulose ester film is thicker than the upper limit of the above range, for example when used as a polarizing plate protecting film, the finished polarizing plate is excessively thick, making it unsuitable for the liquid crystal display units employed in notebook type personal computers and mobile electronic devices. On the other hand, when the thickness is below the lower limit of the above range, it becomes difficult to result in retardation as a retardation film, and further, and water vapor permeability increases, whereby capability of protecting polarizers from moisture is degraded.

Further, in the solution-casting method, an increase in thickness markedly increases drying load. However, in the present invention, no drying process is required, and it is possible to produce quite thick films at high productivity. Due to that, an advantage results in which it is easier than before to increase film thickness depending on purposes such as providing required retardation and a simultaneous decrease in water vapor permeability. Further, effects result in which even though film thickness is low, by stretching such a rather thick film, it is possible to achieve efficient production.

Further, the thickness variation of cellulose ester film supports is preferably within ±3 percent, is more preferably within ±1 percent, but is still more preferably within ±0.1 percent.

The width of the cellulose ester film of the present invention is preferably 1-4 m, but is particularly preferably 1.4-4 m.

Since cellulose ester film, in which the organic acid polyhydric alcohol ester compounds, represented by above Formula (1) of the present invention, are employed as a plasticizer, and result in an optical film which exhibits excellent flatness, it is possible to produce a relatively wide cellulose polyester film. The employed width is preferably 1.4-4 m, but is particularly preferably 1.4-2 m. When the width exceeds 4 m, problems such as shipping difficulty occur.

The length of the rolled film is preferably 500-5,000 m, but is more preferably 1,000-5,000 m. It is also preferable that winding is performed while knurling of a height of 0-25 percent with respect to the film thickness on both edges.

In order to achieve stable production of such a long-length film, it is essential that no volatile components are blended into the casting materials. The casting temperature employing the melt-casting method markedly differs from that of the solution-casting method. Consequently, if volatile components are present, such additives are evaporated during casting and adhere to the casting apparatus, resulting in various problems. Therefore, in view of achieving film flatness and transparency to enable utilization as a film and a polarizing plate protecting film, the presence of such volatile materials is not preferred. Specifically, adhesion onto dies results in streaking on the film surface whereby degradation of flatness is occasionally induced. Consequently, in cases in which film constituting materials are subjected to casting, in view of minimizing the formation of volatile components during heat-melting, it is preferable that no volatile components are present in the range which is lower than the melting temperature for casting.

Listed as the above volatile components are moisture absorbed into any of the film constituting materials, mixed gases such as oxygen or nitrogen, solvents and impurities mixed prior to procurement of materials or during synthesis, as well as evaporated materials via heating and materials derived from sublimation and volatized materials due to decomposition. "Solvents", as described herein, differ from those which dissolve resins to prepare solution as a casting solution. Consequently, selection of film constituting materials is important to avoid the generation of volatile components.

In the present invention, prior to casting or during heating, it is preferable to remove the volatile components represented by the above moisture and solvents from the film constituting materials employed for solution-casting. It is possible to employ, as the above removing method, drying method such as a heating method, a vacuum method, or a heating-vacuum method. Drying may be performed under ambient air or inert gases such as nitrogen or argon. It is preferable that these inert gases incorporate a low or no amount of moisture or water. When these drying methods, known in the art are performed, in view of the film quality, it is preferable that drying is performed in the temperature range in which film constituting materials do not undergo decomposition. For example, after removing moisture or solvents in the above drying process, any residual moisture or solvents is preferably at most 3 percent by weight with respect to the total weight of the constituting materials of each film, but is more preferably at most only 1 percent by weight.

Specifically, the moisture content of employed cellulose ester resins is preferably less than 0.5 percent by weight. It is possible to determine these characteristic values based on ASTM-D817-96. It is further preferable that the cellulose ester is subjected to a decrease in moisture via a heat treatment and employed at a moisture amount of 0.1-1,000 ppm.

By drying film constituting materials prior to casting, it is possible to lower the generation of volatile materials. Resins may be dried individually. Alternately, film constituting materials may be divided into a mixture of at least one except from resins or a compatible material which may be dried. Drying temperature is preferably at least 80° C.–at most the Tg or the melting point of drying materials. In order to also avoid fusion among materials, the drying temperature is more preferably 100° C.–(Tg–5)° C., but is still more preferably 110° C.–(Tg–20)° C. Drying time is preferably 0.5-24 hours, is more preferably 1-18 hours, but is still more preferably 1.5-12 hours. When the drying temperature is below the lower limit, the removal ratio of volatile materials decreases or an excessively long drying time is required. Further, when any of drying materials exhibits Tg, drying, in which the temperature is higher than Tg, difficulty in handling occasionally results due to fusion of materials. It is preferable that drying is performed at most at atmospheric pressure. It is more preferable that particularly, drying is performed under vacuum—½ atmospheric pressure. It is preferable that drying is performed while appropriately mixing materials such as resins. A fluidized bed system is preferred in which in a drying vessel, drying is performed while drying air or nitrogen is being fed from the bottom, since it is possible to achieve required drying within a shorter time.

The drying process may be divided into at least two stages. For example, casting may be performed employing components which have been stored in a preliminary drying process and which have subjected to drying which is performed from immediately to one week prior to casting.

When used as a polarizer protecting film, in-plane retardation value Ro and retardation value Rt in the thickness direction of the cellulose ester film according to the present invention are preferably $0 \leq Ro$ and $Rt \leq 70$ nm, respectively, are more preferably $0 \leq Ro \leq 30$ nm and $0 \leq Rt \leq 50$ nm, but are still more preferably $0 \leq Ro \leq 10$ nm and $0 \leq Rt \leq 30$ nm. When employed as a retardation film, they are preferably $30 \leq Ro \leq 100$ nm and $70 \leq Rt \leq 400$ nm, respectively, but are more preferably $35 \leq Ro \leq 65$ and $90 \leq Rt \leq 180$ nm. Further, the variation of Rt and distribution width are less than ±50 percent, respectively, are more preferably less than ±30 percent, are still more preferably ±20 percent, are further more preferably less than ±20 percent, are still more preferably ±15 percent, are still more preferably ±10 percent, are still further more preferably ±10 percent, are still further more preferably ±5 percent, but are most preferably zero.

It is possible to obtain retardation values Ro and Rt based on the formulas below.

$$Ro = (nx - ny) \times d$$

$$Rt = \{(nx + ny)/2 - nz\} \times d$$

wherein d (in nm) represents the film thickness, nx represents the maximum refractive index on the film plane, (also called the refractive index in the delayed phase axis direction), ny represents the refractive index in the direction at right angles to the delayed phase axis on the film plane, and nz represents the refractive index of the film in the thickness direction.

Further, it is possible to determine retardation values Ro and Rt employing an automatic double refractometer. For example, it is possible to determine them at a wavelength of 590 nm under 23° C. and 55 percent relative humidity, employing KOBRA-21ADH (produced by Oji Scientific Instruments).

Further, the delayed phase axis is preferably within ±1° in the transverse direction or within ±1° in the longitudinal direction, but is more preferably within ±0.7° in the transverse direction or in the longitudinal direction, but is more preferably within ±0.5° in both the transverse and longitudinal directions.

Since solvents are basically not used in the casting process of the cellulose ester film of the present invention, the residual organic solvent amount incorporated in the wound cellulose ester film, after casting, is consistently less than 1 percent by weight. Based on the above, it is possible to provide a cellulose ester film which exhibits more stable flatness and Rt than heretofore. Specifically, in 100 m or longer rolls, it has been possible to produce a cellulose ester film which exhibits stable flatness and Rt. The roll length of the above cellulose ester film is not particularly limited and 1,500, 2,500, and 5,000 m rolls are preferably employed.

It is possible to determine the amount of residual organic solvents employing head space gas chromatography. Namely, cellulose ester film whose amount has been known is heated at 120° C. for 20 minutes in a tightly sealed vessel and organic solvents incorporated in a gas phase in the above tight-sealed vessel are quantitatively analyzed. Based on the results, it is possible to calculate the residual organic solvent amount (in percent).

Further, in cases in which film incorporates moisture, the weight (in g) of the moisture incorporated in the cellulose ester film is determined employing another method. Subsequently, it is possible to obtain a ratio (in percent) of residual organic solvents based on the value obtained by subtracting the weight (in g) of moisture from the weight difference (in g) between prior to and after the above heating treatment.

It is difficult to reach at most 0.1 percent by weight of the residual organic solvent ratio (in percent) in the cellulose ester film prepared employing the solution-casting method. In order to reach the above value, a long drying process is required. However, according to the above method, it is possible to produce a cellulose ester film at a markedly low residual solvent ratio and also to produce a cellulose ester film which exhibits excellent characteristics as an optical film.

Heat-melting constituting materials result in marked decomposition reaction, due to which coloration and quality degradation occasionally result. Further, the decomposition reaction also occasionally generates adverse volatile components.

For the purpose of minimizing modification and moisture absorption of the film constituting materials, pellets composed of at least one of them are prepared and stored. Further, by employing the above pellets, it is possible to prepare a melt. Pelletization serves to enhance mixing properties and compatibility of film constituting materials when melted, and also contributes to achieve optical uniformity of the resulting film. Uniform mixing of constituting material, other than cellulose resins, with the above resins prior to melting makes it possible to contribute to resulting in uniformly melting properties when heat-melted.

In cases employing the cellulose ester film of the present invention as a polarizing plate protecting film while forming a polarizing plate in a liquid crystal display, it is preferable that the polarizing plate on at least one side is the polarizing plate of the present invention, but it is more preferable that both sides are the polarizing plates of the present invention.

Further, employed as conventional polarizing plate protecting film are cellulose ester films such as KONICA MINOLTA TAC KC8UX, KC4UX, KC5UX, KV8UY, KC4UY, KC8UCR-3, KC8UR-4, KC12UR, KC8UXW-H, KC8UYW-HA, or KC8UX-RHA (produced by Konica Minolta Opt, Inc.).

In order to enhance display quality and to provide various desired functions, it is possible to arrange other functioning layers on the polarizing plates employing cellulose ester films of the present invention. For example, arranged may be prior art functional layers such as an antistatic layer, a transparent electric conductive layer, a hard coat layer, an antireflection layer, an anti-staining layer, a lubricating layer, an easy adhesive layer, an anti-glaring layer, or a gas barrier layer. Further, it is possible to arrange an optical anisotropic layer composed of liquid crystals or polyimides. It is possible to achieve optimal compensation via combinations of the polarizing plate protecting film with these optical anisotropic layers. At that time, if desired, it is possible to apply various surface treatments such as a corona discharge treatment, a plasma treatment, or a liquid chemical treatment.

Further, in the cellulose ester films of the present invention, it is possible to prepare a cellulose ester film in a multilayered structure by co-extruding compositions incorporating cellulose ester resins in which the concentrations of additives, such as the aforementioned plasticizer, UV absorber, or matting agent, differ. For example, it is possible to prepare a cellulose ester film structured as a skin layer/core layer/skin layer. For example, it is possible to incorporate minute particles such as a matting agent in the skin layer in a larger amount or only in the skin layer. Further, it is possible to incorporate plasticizers and UV absorbers in the skin layer and in the core layer, but in a larger amount in the core layer, or only in the core layer. Further, it is possible to change the types of plasticizers and UV absorbers in the core layer and also in the skin layer. For example, it is possible to incorporate low volatile plasticizers and/or UV absorbers in the skin layer, and to incorporate plasticizers exhibiting excellent plasticity or UV absorbers exhibiting high absorption of ultraviolet radiation in the core layer. Glass transition temperature of the skin layer and the core layer may differ, and it is possible to arrange the glass transition temperature of the core layer which is lower than that of the skin layer. Further, viscosity of the melt incorporating cellulose esters of the skin layer and the core layer may differ during melt-casting. The following relationship is acceptable: viscosity of the skin layer>viscosity of the core layer≧viscosity of the skin layer.

A long-length cellulose ester film of the present invention is produced employing a melt-casting method. Differing from the solution-casting method, since there are no volatile solvents, melt-casting is an excellent technique in terms of minimal dimensional changes. In the present invention, a long-length film is prepared by continuously apply a stretching process to film produced employing melt-casting.

When a cellulose ester film is subjected to large dimensional variation, the image quality of liquid crystal displays is degraded due to the variation of the optical axis over time. When the dimension of the film which has been allowed to stand at 23° C. and 55 percent relative humidity over 24 hours is determined as a standard, dimensional variation ratio of the film which is stored at 80° C. and 90 percent relative humidity is preferably less than ±0.2 percent, is more preferably less than ±0.1 percent, but is still more preferably less than ±0.05 percent.

Preparation methods of the polarizing plates of the present invention are not particularly limited and common methods are acceptable. It is possible to allow the obtained polarizing plate protecting film, which has undergone an alkaline treatment, to adhere, while employing an aqueous completely saponified polyvinyl alcohol solution, to both sides of a polarizer which is prepared in such a manner that a polyvinyl alcohol film is immersed in an iodine solution, and is then stretched. This method is preferred in which the polarizing plate protecting film of the present invention is made directly adhered to at least one side of a polarizer.

Further, instead of the above alkaline treatment, the polarizing plate protecting film is subjected to an easy adhesion treatment, described in JP-A Nos. 6-94915 and 6-118232, and subsequently, a polarizing plate may be prepared.

A polarizing plate is composed of a polarizer and protective films which protect both its sides. Further, it is possible to allow a protective film to adhere to one side of the above polarizing plate and to allow a separate film on the other side of the same. The protective film and separate film are employed to protect the polarizing plate during shipment and transportation. In this case, the protective film adheres to the polarizing plate to protect it, and adheres to the surface opposite the surface to which a liquid crystal plate adheres. Further, a separate film is employed to cover an adhesive layer.

(Liquid Crystal Display)

A liquid crystal display composed of the polarizing plate incorporating the cellulose ester film of the present invention enables realization of high display quality due to excellent flatness of the cellulose ester film used in the polarizing plate. Specifically, application to a multi-domain type liquid crystal display, more preferably to a multi-domain type liquid crystal display under a birefringence mode enables the desired effects of the present invention to be further exhibited.

Application to the multi-domain type crystal display is suitable to enhance symmetry of the image display and various such systems are reported by Okita and Yamauch i, Ekisho (Liquid Crystal) 6(3), 303 (2002). Liquid crystal cells are also reported by Yamada and Yamahara in Ekisho (Liquid Crystal), 7(2), 184 (2003), however they are not limited thereto.

It is possible to effectively apply the polarizing plate to the MVA (Multi-Domain Vertical Alignment) mode represented by a vertical alignment mode, especially a four-division mode, a prior art PVA (Patterned Vertical Alignment) mode which is subjected to a multi-domain, or a CPA (Continuous Pinwheel Alignment) mode in which electrode arrangement and chirality are integrated. Further, in the application to an OCB (Optical Compensated Bend) mode, a proposal of optically biaxial film is proposed in T. Miyashita and T. Uchida, J. SID, 3(1), 29 (1995), and it is possible to result in effects of the present invention in the display quality employing the polarizing plate according to the present invention. If it is possible to result in the effects of the present invention by employing the polarizing plate of the present invention, the crystal mode and arrangement of polarizing plates are not limited.

Liquid crystal displays have been subjected to color image formation and are being applied to moving image display units. Display quality in the present invention is subjected to improvement in contrast, and the durability of polarizing plates is enhanced. As a result, fatigue decreases and it is possible to faithfully reproduce moving images.

EXAMPLES

The present invention will now be described with reference to examples, however the present invention is not limited thereto.

Cellulose Ester 1 and plasticizers employed in Examples 1-3 were syn1.

Synthesis Example 1

Synthesis of Cellulose Ester 1

Synthesis was performed with reference to Example B of Japanese Patent Application for Public Inspection (PCT Application) No. 6-501040. Mixed Solutions A-E below were prepared.
A: propionic acid:concentrated sulfuric acid=5:3 (weight ratio)
B: acetic acid:pure water=1:1 (weight ratio)
C: acetic acid:pure water=1:1 (weight ratio)
D: acetic acid:pure water:magnesium carbonate=12:11:1 (weight ratio)
E: aqueous solution prepared by dissolving 0.5 mol of potassium carbonate and 1.0 mol of citric acid in 14.6 kg of pure water Charged into a reaction vessel fitted with a mechanical stirrer were 100 parts by weight of purified cotton cellulose, 317 parts by weight of acetic acid, and 67 parts by weight of propionic acid, the resulting mixture was stirred at 55° C. for 30 minutes. After lowering the temperature of the reaction vessel to 30° C., 2.3 parts by weight of Solution A were added and the resulting mixture was stirred for 30 minutes. After cooling the reaction vessel to −20° C., 100 parts by weight of acetic anhydride and 250 parts by weight of propionic anhydride were added and the resulting mixture was stirred for one hour. After raising the temperature of the reaction vessel to 10° C., 4.5 parts by weight of Solution A were added and the resulting mixture was heated to 60° C. and then stirred for 3 hours. In addition, 533 parts by weight of Solution B were added and the resulting mixture was stirred for 17 hours. Further added were 333 parts by weight of Solution C and 730 parts by weight of Solution D and stirring was performed for 15 minutes. Insoluble materials were collected by filtration, and while stirring, water was added to the filtrate until the completion of the formation of white precipitates. Thereafter, the resulting white precipitates were collected by filtration. The resulting white solids were washed with pure water until the washing water was neutral. Added to the resulting wet product were 1.8 parts by weight of Solution E, and subsequently, dried under vacuum at 70° C. for 3 hours, whereby cellulose acetate propionate was obtained.

The degree of substitution of the resulting cellulose acetate propionate was calculated based on ASTM-D817-96. The degree of substitution due to the acetyl group was 1.9, while the same due to the propionyl group was 0.7. Further, GPC was determined under the conditions below, resulting a molecular weight of 200,000.

(GCP Determination Conditions)
Solvent: methylene chloride
Columns: SHODEX K806, K805, and K803 (produced by Showa Denko
  K.K., three columns were connected and employed)
Column temperature: 25° C.

Sample concentration: 0.1 percent by weight
Detector: RI Model 504 (produced by GL Science Co.)
Pump: L6000 (produced by Hitachi Ltd.)
Flow rate: 1.0 ml/minute

Synthesis Example 2

Synthesis of Comparative Example Compound Trimethylolpropane Tribenzoate (TMPTB)

While stirring, 71 parts by weight of benzoyl chloride were dripped over 30 minutes to a mixed solution of 45 parts by weight of trimethylolpropane and 101 parts by weight of triethylamine maintained at 100° C., and the resulting mixture was stirred for an additional 30 minutes. After completion of the reaction, the temperature was lowered to room temperature and the resulting precipitates were collected by filtration. Thereafter, washing was performed by adding ethyl acetate-pure water. Subsequently, the organic phase was collected and ethyl acetate was distilled out under vacuum, whereby 126 parts by weight (at a yield of 85 percents) of white crystals were obtained. The molecular weight of the resulting compound was 446.

Synthesis Example 3

Synthesis of Compound Example 2 in the Example

While stirring, 180 parts by weight of monomethyl phthalate, one part by weight of dimethylformamide, and 130 parts by weight of thionyl chloride were mixed at 60° C. for 30 minutes. After completion of the reaction, the reaction product was cooled, whereby a pale yellow liquid was obtained.

The pale yellow liquid, prepared as above, was dripped at room temperature over 30 minutes into a solution incorporating 31 parts by weight of glycerin, 101 parts by weight of triethylamine, and 200 parts by weight of ethyl acetate, and stirring was continued for an additional one hour. The resulting white precipitates were collected by filtration and the resulting precipitates were washed with pure water, and the organic phase was collected. Thereafter, organic solvents were distilled out under vacuum, whereby 116 parts by weight (at a yield of 60 percent) of white crystals were obtained. The molecular weight of the resulting compound was 579.

Synthesis Example 4

Synthesis of Comparative Example Compound, Pentaerythritol Tetrapivalate (PETP)

Pentaerythritol tetrapivalate which was employed in examples as PL2 in Patent Document 5, was synthesized.

At room temperature, 121 parts by weight of pivaloyl chloride were dripped over 30 minutes into a solution consisting of 34 parts by weight of pentaerythritol, 101 parts by weight of triethylamine, and 2,000 parts by weight of ethyl acetate, and the resulting mixture was stirred for an additional one hour. The resulting white precipitates were collected by filtration, and washed with pure water. After collecting the organic phase, organic solvents were distilled out under vacuum, whereby 89 parts by weight (at a yield of 75 percent) of white crystals were obtained The molecular weight of the resulting compound was 473.

Synthesis Example 5

Synthesis of Exemplified Compound 20

A mixture was prepared by mixing 136 parts by weight of pentaerythritol, 1,070 parts by weight of phenyl salicylate, and 2 parts by weight of potassium carbonate. The resulting mixture was maintained at 155° C. for 3 hours under $1.333 \times 10^{-2}$ Mpa, and 375 parts by weight of phenol were distilled out. After returning the pressure of the reaction vessel to normal pressure, the temperature was lowered to 100° C. and 1 part by weight of concentrated sulfuric acid and 450 parts by weight of acetic anhydride were added and the resulting mixture was stirred at 100° C. for one hour. After completion of the reaction, 2,000 parts by weight of toluene were added and the resulting mixture was ice-cooled, whereby white crystals were formed. The resulting white crystals were collected by filtration, washed twice with pure water, and subsequently subjected to vacuum drying at 30° C., whereby 667 parts by weight (at a yield of 85 percent) of white crystals were obtained. The molecular weight of the resulting compound was 785.

Synthesis Example 6

Synthesis of Comparative Example Compound Sorbitol Hexabenzoate (SHB)

While stirring, 71 parts by weight of benzoyl chloride were dripped over 30 minutes into a mixed solution of 30 parts by weight of sorbitol and 101 parts by weight of triethylamine maintained at 100° C., and the resulting mixture was stirred for an additional 30 minutes. After completion of the reaction, the temperature was lowered to room temperature, and the resulting precipitates were collected by filtration. Thereafter, washing was performed by adding ethyl acetate-pure water. Subsequently, the organic phase was collected and ethyl acetate was distilled out under vacuum, whereby 100 parts by weight (at a yield of 74 percent) of white crystals were obtained. The molecular weight of the resulting compound was 809.

Synthesis Example 7

Synthesis of Example Compound Exemplified Compound 33

A mixture was prepared by blending 182 parts by weight of sorbitol, 1,607 parts by weight of phenyl salicylate, and 2 parts by weight of potassium carbonate. The resulting mixture was heated at 155° C. for 3 hours under $1.333 \times 10^{-2}$ MPa, and 565 parts by weight of phenol were distilled out. After returning the pressure of the reaction vessel to normal pressure, the temperature was lowered to 100° C. and 1 part by weight of concentrated sulfuric acid and 675 parts by weight of acetic anhydride were added and the resulting mixture was stirred at 100° C. for one hour. After completion of the reaction, 2,000 parts by weight of toluene were added and the resulting mixture was ice-cooled, whereby white crystals were formed. The resulting white crystals were collected by filtration, washed twice with pure water, and subsequently subjected to vacuum drying at 40° C., whereby 925 parts by weight (at a yield of 80 percent) of white crystals were obtained. The molecular weight of the resulting compound was 1,155.

Synthesis Example 8

Synthesis of Example Compound Exemplified Compound 9

While stirring, 240 parts by weight of o-methoxybenzoyl chloride were dripped over 30 minutes into a mixed solution of 54 parts by weight of trimethylolpropane, 127 parts by weight of pyridine, and 500 parts by weight of ethyl acetate maintained at 10° C. Thereafter, the resulting mixture was heated to 80° C. and was stirred for 3 hours. After completion of the reaction, the temperature was lowered to room temperature and the resulting precipitates were collected by filtration. Thereafter, washing was performed by adding 1N aqueous HCl solution and further by adding 1 percent aqueous $Na_2CO_3$ solution. Subsequently, the organic phase was collected and ethyl acetate was distilled out under vacuum, whereby 193 parts by weight (at a yield of 90 percent) of a transparent liquid was obtained. The molecular weight of the resulting compound was 537.

Synthesis Example 9

Synthesis of Example Compound Exemplified Compound 7

While stirring, a solution prepared by dissolving 180 parts by weight of acetylsalicyloyl chloride in 200 parts by weight of ethyl acetate was dripped over 30 minutes into a mixed solution of 27 parts by weight of trimethylolpropane, 111 parts by weight of pyridine, and 300 parts by weight of ethyl acetate maintained at 10° C. Thereafter, the resulting mixture was heated to 80° C. and was stirred for 3 hours.

After completion of the reaction, the temperature was lowered to room temperature and the resulting precipitates were collected by filtration. Thereafter, washing was performed by adding 1N aqueous HCl solution and further by adding 1 percent aqueous $Na_2CO_3$ solution. Subsequently, the organic phase was collected and ethyl acetate was distilled out under vacuum, whereby 99 parts by weight (at a yield of 80 percent) of a transparent liquid was obtained. The molecular weight of the resulting compound was 621.

Synthesis Example 10

Synthesis of Example Compound Exemplified Compound 45

While stirring, a solution prepared by dissolving 217 parts by weight of 3,4-dimuthoxybenzoyl chloride in 300 parts by weight of ethyl acetate was dripped over 30 minutes into a mixed solution of 36 parts by weight of trimethylolpropane, 107 parts by weight of pyridine, and 300 parts by weight of ethyl acetate maintained at 10° C. Thereafter, the resulting mixture was heated to 80° C. and was stirred for 5 hours.

After completion of the reaction, the temperature was lowered to room temperature and the resulting precipitates were collected by filtration. Thereafter, washing was performed by adding a 1N aqueous HCl solution and further by adding a 1 percent aqueous $Na_2CO_3$ solution. Subsequently, the organic phase was collected and ethyl acetate was distilled out under vacuum, whereby 135 parts by weight (at a yield of 80 percent) of a transparent liquid was obtained. The molecular weight of the resulting compound was 627.

Synthesis Example 11

Synthesis of Example Compound Exemplified Compound 48

While stirring, a solution prepared by dissolving 250 parts by weight of 3,4,5-tromethoxybenzoyl chloride in 300 parts by weight of ethyl acetate was dripped over 30 minutes into a mixed solution of 36 parts by weight of trimethylolpropane, 107 parts by weight of pyridine, and 300 parts by weight of ethyl acetate maintained at 10° C. Thereafter, the resulting mixture was heated to 80° C. and was stirred for 5 hours.

After completion of the reaction, the temperature was lowered to room temperature and the resulting precipitates were collected by filtration. Thereafter, washing was performed by adding a 1N aqueous HCl solution and further by adding a 1 percent aqueous $Na_2CO_3$ solution. Subsequently, the organic phase was collected and ethyl acetate was distilled out under vacuum, whereby 153 parts by weight (at a yield of 80 percent) of white precipitates were obtained.

The molecular weight of the resulting compound was 717.

Example 1

By employing the various compounds synthesized in above Synthesis Examples and various commercially available compounds as a plasticizer, powders which were prepared by blending the compounds below at the blending ratio below were charged into a biaxial extruder, and a melt-casting was conducted. However, additives which were in liquid form at normal temperature were added employing a feeder immediately prior to being fed into a biaxial kneading section.

<Preparation of Films 101-118>

| | |
|---|---|
| Cellulose acetate proionate (Cellulose Ester 1) | 100 parts by weight |
| Plasticizer described in Table 1 | amount as indicated in Table 1 |
| LA 31 (UV absorber) | 1.0 part by weight |
| IRUGANOX 1010 (antioxidant) | 0.5 part by weight |
| SUMILIZER GP (antioxidant) | 3.0 part by weight |
| Epoxidized Soybean Oil (acid scavenger) | 1.0 part by weight |
| AEROSIL R972V (matting agent) | 0.3 part by weight |

In Table 1, CHEM 1, and the like refer to the Exemplified Compound number, and various comparative compounds are as follows.

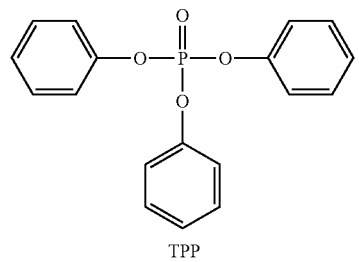

TPP

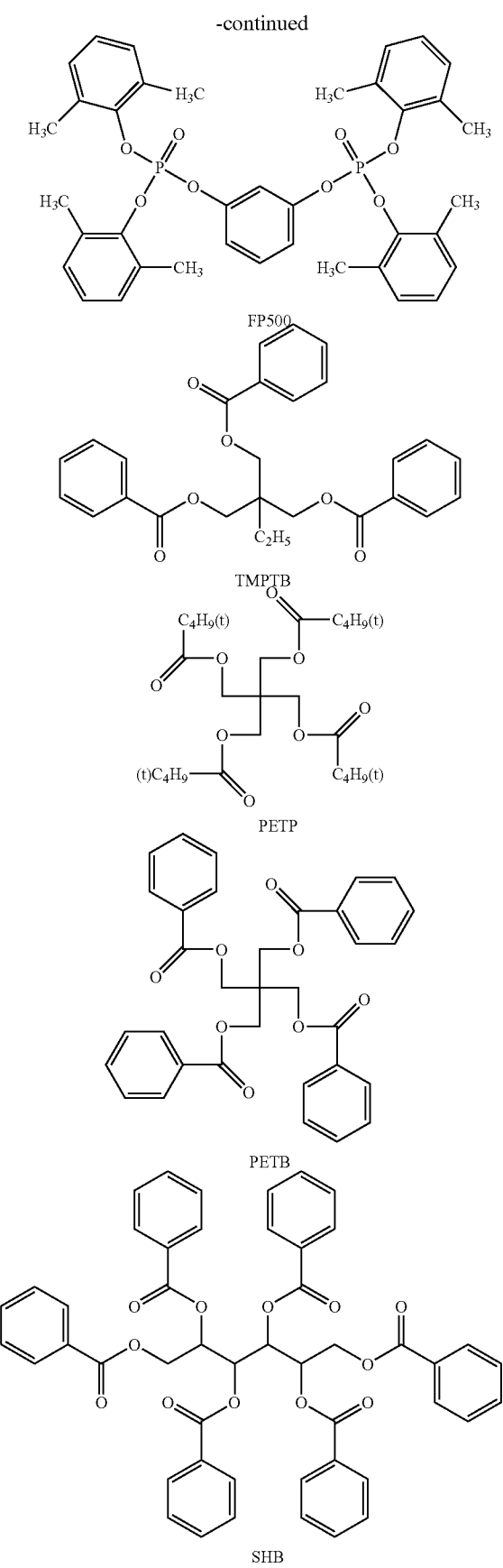

Melt-casting conditions included a rotation rate of 200 rpm, a barrel temperature of 240° C., a casting drum temperature of 90° C., and melt-casting was performed to achieve a resulting film thickness of 80 μm. Further, employed were cellulose esters which had been dried at 70° C. for 3 hours under vacuum. The structures of compounds used for comparison are as follows. TPP is the abbreviation for triphenyl phosphate, while PETB is the abbreviation for pentaerythritol tetrabenzoate, both of which were procured from Aldrich. Further, FP500 was procured from Asahi Denka K.K.

Resulting Cellulose Ester Films 101-118 were subjected to the evaluation below.

<<Determination of Water Vapor Permeability>>

Water vapor permeability was determined based on the method described in JIS Z 0208. Conditions during determination were 40° C. and 90 percent relative humidity.

<<Evaluation of Dimensional Stability and Bleeding-Out>>

Each cellulose ester sample was cut to a size of 150 mm in the transverse direction×120 mm in the longitudinal direction, and the surface of the above cellulose derivative film was subjected to two cross type marks employing a razor blade at an interval of 100 mm in the transverse direction (TD) and the longitudinal direction (MD). The resulting cellulose ester film was rehumidified at 23±3° C. and 55±3 percent relative humidity for at least 24 hours. Thereafter, distance L0 between the cross marks was determined employing a microscope. Subsequently, the resulting sample was allowed to stand for two weeks and then rehumidified again at 23±3° C. and 55±3 percept relative humidity, which were the same as above, for 24 hours. Then, distance L1 between the cross marks of the resulting film was determined, employing a microscope. Dimensional variation ratio L1 (in percent) in each of the transverse direction (TD) and the longitudinal direction (MD) was obtained based on the following formula.

Dimensional variation ratio (in percent)=$\{(L1-L0)/L0\}\times 100$

Further, in order to evaluate the bleeding-out property, the film which had been rehumidified at 23° C. and 55 percent relative humidity after removing from a high temperature and high humidity ambience was subjected to a wiping test employing a rag and a felt pen bleeding test. The film surface was wiped and if marks remained after wiping, the film evaluated as C. The film surface was written on with a felt pen, and when bleeding resulted, the film was evaluated as C. When neither resulted, the film was evaluated as A. When any one of them resulted slightly, the film was evaluated as B.

<<Determination of Yellow Index (YI)>>

Absorption spectra of the resulting cellulose ester film was determined employing spectrophotometer U-3310, produced by Hitachi High Technologies Co., and tristimulus values were calculated. Employing the above tristimulus values, Yellow Index YI was calculated based on JIS K 7103.

<<Evaluation of Flatness>>

A sample was collected one hour after the initiation of melt-casting, and the sample size was 100 cm in length×40 cm in width.

A black sheet of paper was pasted on a flat desk and the resulting sample was placed on the sheet. Three fluorescent lamps arranged obliquely upward were reflected on the film surface and flatness was evaluated by observing the degree of curving of the image of the fluorescent lamp. Ranking was performed based on the following criteria.

A: all three fluorescent lamps looked straight
B: fluorescent lamps looked slightly curved
C: fluorescent lamps looked clearly curved
D: fluorescent lamps looked significantly winding Table 1 shows the results.

TABLE 1

| No. | Plasticizer Type | Added Amount | *1 | *2 | *3 | YI | Dimensional Stability (%) MD | TD | *4 | Remarks |
|---|---|---|---|---|---|---|---|---|---|---|
| 101 | TPP | 10% | 326 | 540 | C | 6.5 | 0.22 | 0.19 | C | Comp. |
| 102 | FP500 | 10% | 686 | 520 | C | 3.7 | 0.10 | 0.09 | D | Comp. |
| 103 | CHEM 1 | 10% | 494 | 510 | A | 1.0 | 0.09 | 0.10 | B | Inv. |
| 104 | CHEM 3 | 10% | 579 | 510 | A | 1.0 | 0.08 | 0.09 | B | Inv. |
| 105 | CHEM 5 | 10% | 523 | 510 | A | 1.0 | 0.09 | 0.08 | B | Inv. |
| 106 | CHEM 1 | 15% | 494 | 500 | A | 1.0 | 0.09 | 0.08 | B | Inv. |
| 107 | TMPTB | 10% | 446 | 520 | B | 1.0 | 0.09 | 0.08 | D | Comp. |
| 108 | CHEM 2 | 10% | 579 | 500 | A | 1.0 | 0.07 | 0.07 | B | Inv. |
| 109 | TMPTB | 5% | 446 | 510 | A | 1.0 | 0.07 | 0.08 | C | Inv. |
|  | CHEM 2 | 5% | 579 |  |  |  |  |  |  |  |
| 110 | PETB | 10% | 553 | 510 | C | 1.0 | 0.06 | 0.07 | D | Comp. |
| 111 | PETP | 10% | 473 | 870 | B | 1.0 | 0.12 | 0.12 | D | Comp. |
| 112 | CHEM 20 | 10% | 785 | 480 | A | 1.0 | 0.05 | 0.05 | B | Inv. |
| 113 | SHB | 10% | 809 | 500 | C | 1.0 | 0.05 | 0.05 | D | Comp. |
| 114 | CHEM 33 | 10% | 1155 | 490 | A | 1.0 | 0.05 | 0.05 | C | Inv. |
| 115 | CHEM 9 | 10% | 537 | 490 | A | 1.0 | 0.05 | 0.04 | A | Inv. |
| 116 | CHEM 7 | 15% | 621 | 460 | A | 1.0 | 0.04 | 0.04 | A | Inv. |
| 117 | CHEM 45 | 10% | 627 | 500 | A | 1.0 | 0.06 | 0.07 | B | Inv. |
| 118 | CHEM 48 | 20% | 717 | 500 | A | 1.0 | 0.07 | 0.07 | B | Inv. |

*1 Molecular Weight,
*2: Water Vapor Permeability g/m$^2$/d,
*3: Bleeding-Out,
*4: Flatness Evaluation,
Comp.: Comparative Example,
Inv.: Present Invention As can clearly be seen from Table 1, Film 111, in which polyhydric alcohol-alkylcarboxylic acid ester was employed, was not preferable due to its high water vapor permeability. On the other hand, even though the water vapor permeability was reduced to be at most 550 g/m$^2$/d, Films 107, 110 and 113, in which polyhydric alcohol-alkylcarboxylic acid ester was employed, were not preferable due to poor film flatness. Further, they tended to result in bleeding-out.

On the other hand, Example Films 103-106, 108, 112, and 114-118 in which polyhydric alcohol-alkylcarboxylic acid ester was employed, were preferable since water vapor permeability was retarded to be low whereby no bleeding-out resulted and the flatness was improved.

When the molecular weight exceeded 1,000, flatness improving effects were lower. Consequently, it was found that the molecular weight of the polyhydric alcohol ester compounds was preferably 400-1,000. Further, the compounds of the present invention exhibited high compatibility with cellulose esters, whereby it was possible to incorporate them at a high content ratio. Even by simultaneously employing the other compounds, which exhibited low compatibility (being Film 110), it was possible to result in fixed effects.

Further, Films 101 and 102, in which phosphoric acid based esters were employed, were not preferable due to coloration via melt-casting. Further, by employing phosphoric acid based esters having a substituent on the aromatic group, improved flatness effects, which were noted in the compounds of the present invention, were not exhibited.

Example 2

Cellulose Ester Films 201-205 were prepared by performing melt-casting in the same manner as for Example 1, except that while Exemplified Compound 48 was employed as a plasticizer in all films, cellulose esters were replaced as shown in Table 2.

Further, all the cellulose esters 2-5, other than cellulose esters 1 which was prepared in Synthesis Example 1, were prepared in the same manner as Synthesis Example 1 and controlling the degree of acyl substitution. The molecular weight of all of them was about 200000.

The melting temperature was set at the lowest temperature at which it was possible for each cellulose ester to perform melt-casting. Table 2 also shows each of tar melting temperatures.

Resulting Films 201-205 were evaluated in the following manner.

<<Determination of Elastic Modulus>>

Each of Samples 201-205 prepared as above was cut to 10 mm in the traverse direction (the MD direction) by 200 mm in the moving direction (the MD direction). After rehumidifying the cut samples at 23° C. and 55 percent relative humidity, the upper and lower edges of the sample film in the moving direction (the MD direction) were chuck-fixed employing TENSIRON (RTA-100) produced by Orientec Co. and the distance between the chucks was set at 100 mm intervals. Subsequently, the resulting sample film was pulled at a rate of 100 mm/minute and the elastic modulus (in GPa) in the MD direction was determined. A larger value shows that strength against pulling was higher.

Further, bleeding-out and flatness were evaluated in the same manner as for Example 1.

TABLE 2

| No. | Cellulose Ester Type | X | Y | X + Y | *1 | *2 | Flatness | Elastic Modulus | Remarks |
|---|---|---|---|---|---|---|---|---|---|
| 201 | Cellulose Ester 1 | 1.9 | 0.7 | 2.6 | 240 | B | B | 3.0 GPa | Inv. |

TABLE 2-continued

| | Cellulose Ester | | | | | | Elastic | |
|---|---|---|---|---|---|---|---|---|
| No. | Type | X | Y | X + Y | *1 | *2 | Flat- ness | Modu- lus | Re- marks |
| 202 | Cellulose Ester 2 | 0.2 | 2.6 | 2.8 | 230 | C | B | 1.4 GPa | Inv. |
| 203 | Cellulose Ester 3 | 1.7 | 1 | 2.7 | 240 | B | B | 2.7 GPa | Inv. |
| 204 | Cellulose Ester 4 | 1.6 | 1.2 | 2.8 | 220 | B | B | 2.6 GPa | Inv. |
| 205 | Cellulose Ester 5 | 1.5 | 1.3 | 2.8 | 200 | B | B | 2.5 GPa | Inv. |

*1: Melting Temperature (° C.),
*2: Bleeding-Out
Inv.: Present Invention,
X: degree of acetyl substitution
Y: degree of propionyl substitution As can clearly be seen from Table 2, by substituting aromatic carboxylic acid of polyhydric alcohol-aromatic carboxylic acid esters, compatibility varied, whereby when cellulose ester was employed in which substitution degree (Y) by a propionyl group was at most 2.0, polyhydric alcohol-aromatic carboxylic acid ester exhibited higher compatibility. Further, when cellulose ester was used in which substitution degree (Y) by a propionyl group was at most 2.0, a preferred elastic modulus resulted. Thus, it was possible to prepare the preferred films.

Example 3

(Preparation of Polarizing Plates)
Subsequently, Cellulose Ester Films 101-118, prepared as above, were subjected to the alkaline saponifying process below and each of Polarizing Plates 101-118 was prepared.

(Alkaline Saponifying Treatment)

| Saponifying Process | 2 mol/L NaOH | 50° C. 90 sec. |
|---|---|---|
| Washing Process | water | 30° C. 45 sec. |
| Neutralizing Process | 10 weight % HCl | 30° C. 45 sec. |
| Washing Process | water | 30° C. 45 sec. |

After the saponifying process, washing, neutralization, and washing were performed in the described order, and the resulting film was dried at 80° C.

(Preparation of Polarizers)
A 120 μm thick long-length polyvinyl alcohol film was immersed into 100 parts by weight of an aqueous solution incorporating 1 part by weight of iodine and 4 parts by weight of boric acid, and then stretched at 50° C. by a factor of 6 in the moving direction, whereby a polarizer was prepared.

The cellulose ester film, prepared as above, adhered to both sides of the above polarizer to have the alkaline saponified side face the polarizer side, employing a 5 percent aqueous completely saponified type polyvinyl alcohol solution as an adhesive, whereby a polarizing plate was prepared in which a polarizing plate protecting film was subjected to adhesion.

(Evaluation of Characteristics as Liquid Crystal Display)
The polarizing plate of TYPE 32 TFT TYPE COLOR LIQUID CRYSTAL DISPLAY VEGA (produced by Sony Corp.) was peeled. Subsequently, each of the polarizing plates prepared as above was cut to match the size of the liquid crystal cell. Two polarizing plates, prepared as above, adhered so as to interpose the liquid crystal cell so that the polarizing axes of the above two polarizing plates were at right angles to each other while the polarizing axis of the polarizing plate was the same as before, whereby a TYPE 32 TFT TYPE color liquid crystal display was prepared and the characteristics as a cellulose ester film polarizing plate were evaluated. The polarizing plate of the present invention resulted in high contrast and exhibited excellent display properties. Based on the above, it was confirmed that the polarizing plate prepared by using a cellulose film of the present invention was an excellent polarizing plate for image display units such as a liquid crystal display.

What is claimed is:

1. A cellulose ester film comprising a plasticizer represented by Formula (2) in an amount of 1 to 25 weight % based on the total weight of the cellulose ester film:

Formula (2)

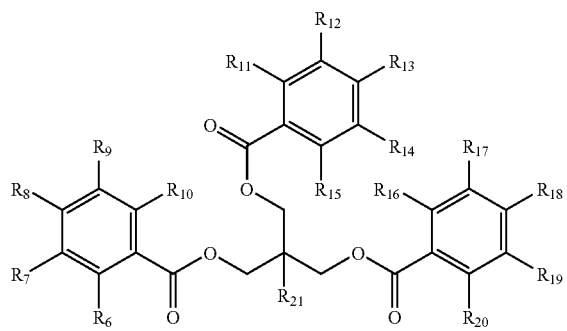

wherein $R_6$ to $R_{20}$ each independently represent a hydrogen atom, a cycloalkyl group, an aralkyl group, an alkoxy group, a cycloalkoxy group, an aryloxy group, an aralkyloxy group, an acyl group, a carbonyloxyl group, an oxycarbonyl group or an oxycarbonyloxy group, provided that $R_6$ to $R_{20}$ may have further a substituent; and at least one of $R_6$ to $R_{10}$, at least one of $R_{11}$ to $R_{15}$ and at least one of $R_{16}$ to $R_{20}$ each is not a hydrogen atom; and $R_{21}$ represents an alkyl group; wherein the cellulose ester film satisfies the following Relationship (2) and Relationship (3), $$2.5 \leq X+Y \leq 2.9 \quad \text{Relationship (2)}$$

$$0.1 \leq Y \leq 2.0 \quad \text{Relationship (3)}$$

wherein X is a degree of substitution with acetic acid and Y is a degree of substitution with an aliphatic acid having 3 to 5 carbon atoms.

2. The cellulose ester film of claim 1, wherein at least one of $R_6$ to $R_{10}$, at least one of $R_{11}$ to $R_{15}$, and at least one of $R_{16}$ to $R_{20}$ each is a methoxy carbonyl group (—C(=O)—OCH$_3$) group.

3. The cellulose ester film of claim 1, wherein at least one of $R_6$ to $R_{10}$, at least one of $R_{11}$ to $R_{15}$, and at least one of $R_{16}$ to $R_{20}$ each is a methoxy group (—OCH$_3$).

4. The cellulose ester film of claim 1, produced by a melt casting film forming method.

5. The cellulose ester film of claim 1, further comprising an anti-oxidizing agent in the film.

6. The cellulose ester film of claim 1, further comprising an acid scavenger in the film.

7. The cellulose ester film of claim 1, further comprising a UV absorbing agent in the film.

8. A liquid crystal display comprising the polarizing plate of claim 7.

9. A polarizing plate comprising the cellulose ester film of claim 1 as a protective film on the polarizing plate.

* * * * *

UNITED STATES PATENT AND TRADEMARK OFFICE
CERTIFICATE OF CORRECTION

| | | |
|---|---|---|
| PATENT NO. | : 7,569,259 B2 | Page 1 of 1 |
| APPLICATION NO. | : 11/294493 | |
| DATED | : August 4, 2009 | |
| INVENTOR(S) | : Okubo et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 603 days.

Signed and Sealed this

Seventh Day of September, 2010

David J. Kappos
*Director of the United States Patent and Trademark Office*